(12) United States Patent
Elmaleh et al.

(10) Patent No.: US 6,835,371 B1
(45) Date of Patent: Dec. 28, 2004

(54) DIAGNOSTIC AND THERAPEUTIC PIPERAZINE AND PIPERIDINE COMPOUNDS AND PROCESS

(76) Inventors: David R. Elmaleh, 38 Hartman Rd., Newton, MA (US) 02159; Choi Sung-Woon, 68 Mechanic St., Canton, MA (US) 02021

( * ) Notice: Subject to any disclaimer, the term of this patent is extended or adjusted under 35 U.S.C. 154(b) by 663 days.

(21) Appl. No.: 09/633,482

(22) Filed: Aug. 7, 2000

Related U.S. Application Data

(60) Continuation-in-part of application No. 09/431,059, filed on Nov. 1, 1999, now Pat. No. 6,251,363, which is a division of application No. 08/928,246, filed on Sep. 12, 1997, now Pat. No. 6,001,330.

(51) Int. Cl.$^7$ ............................................... A61K 49/00

(52) U.S. Cl. ...................... 424/9.1; 424/1.11; 424/1.65; 514/188; 514/277; 514/315; 548/400

(58) Field of Search ............................ 424/1.11, 1.45, 424/1.37, 1.65, 9.1, 9.3, 9.4, 9.5, 9.6, 9.7, 9.8; 548/400, 416, 427; 514/188, 277, 315

(56) References Cited

U.S. PATENT DOCUMENTS 6,001,330 A * 12/1999 Elmaleh et al. ............ 424/1.45
6,251,363 B1 * 6/2001 Elmaleh et al. ............ 424/1.45

* cited by examiner

*Primary Examiner*—Dameron L. Jones

(57) ABSTRACT

Piperazine or piperidine compounds useful for treating neurodegenerated diseases characterized by the lack of dopamine neurons activity or for imaging the dopamine neurons are provided. The piperazine or piperadine compounds are characterized by the formula: Formula I

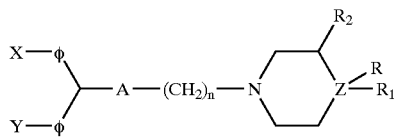

wherein:
A is oxygen; n is an integer of 1 to 6; X and Y can be the same or different and are hydrogen, halogen, nitro, alkyl or halalkyl, Z is carbon or nitrogen; and φ is phenyl, naphthyl, thienyl or pyridinyl.

When Z is carbon, R is hydrogen, cyano, hydroxy, —COOCH$_3$, —CH$_2$OH or —COOH; R$_1$ is 4-fluorophenyl, 4-chlorophenyl, 4-trifluoromethyl, 3-trifluoromethyl-4 -chlorophenyl 4-bromophenyl), 4-(2-keto-1-benzimidazolinyl or 1-phenyl 1, 3, 8-triazaspiro [4,5] decan-4-one. When Z is nitrogen, R and R$_1$ combined are

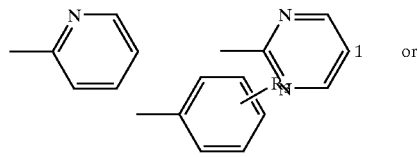

wherein R$_3$ is halo, alkyl, cyano or nitro and R$_2$ can be hydrogen or

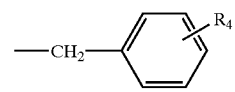

wherein R$_4$ is halo, alkyl, cyano, nitro, alkylnyl or alkenyl Scheme 1

-continued
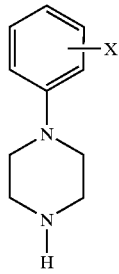
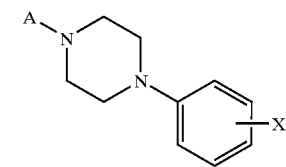
3B
K$_2$CO$_3$/KI
6 X = 2F    31526
7 X = 4F    31527
8 X = 3-CF$_3$  31532
-continued
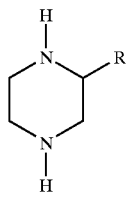
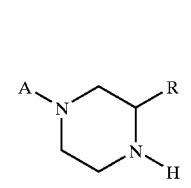
3C
K$_2$CO$_3$/KI
9 R = O     31524
10 R = C$_6$H$_5$  31533.
11 Claims, 17 Drawing Sheets

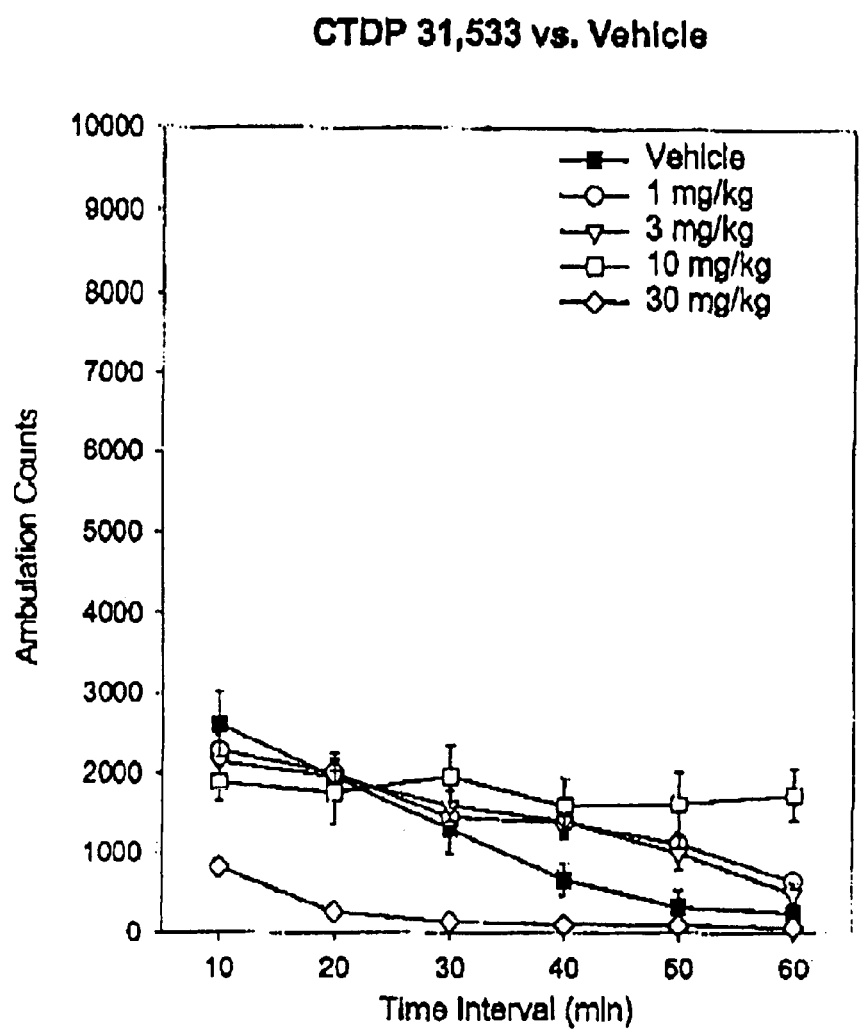
Figure 1 Time course of effects of 31,533 on horizontal activity counts/10 min.

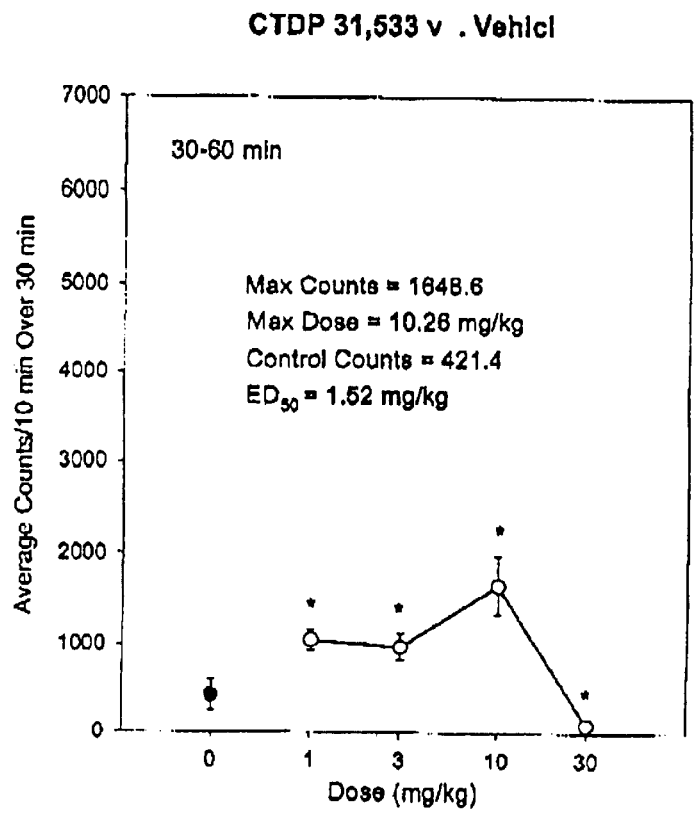
Figure 2  Dose response effects of 31,533 on horizontal activity counts/10 min (30-60 min following injection).
  *$p < 0.05$ compared with 0 dose

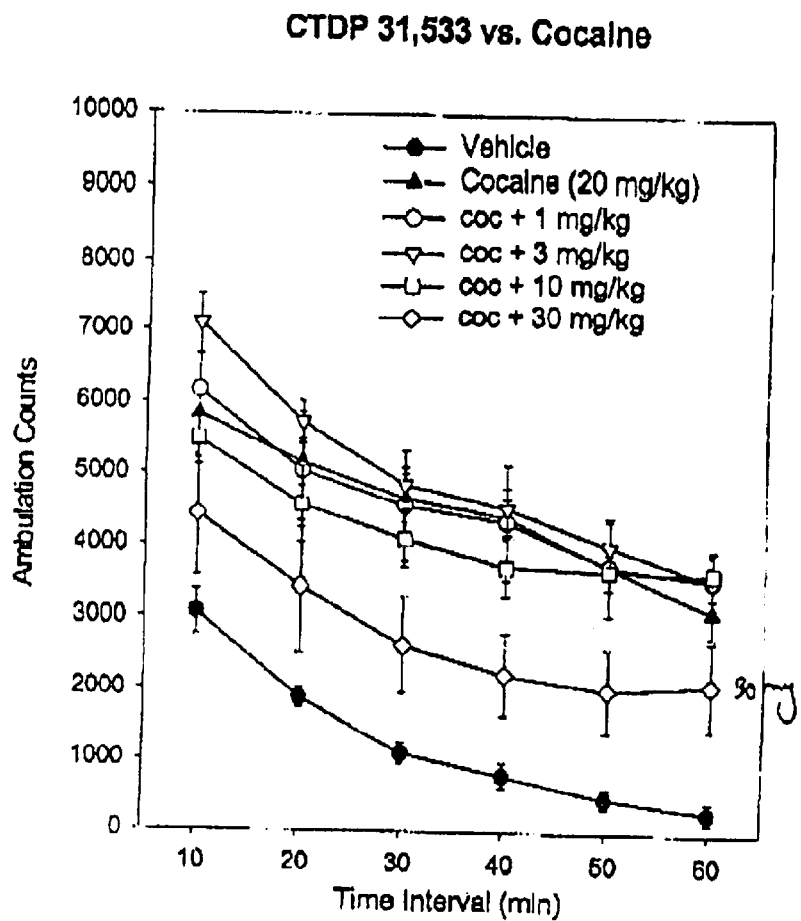
Figure 3 Interaction between 31,533 and cocaine on LMA; Time course of effect.

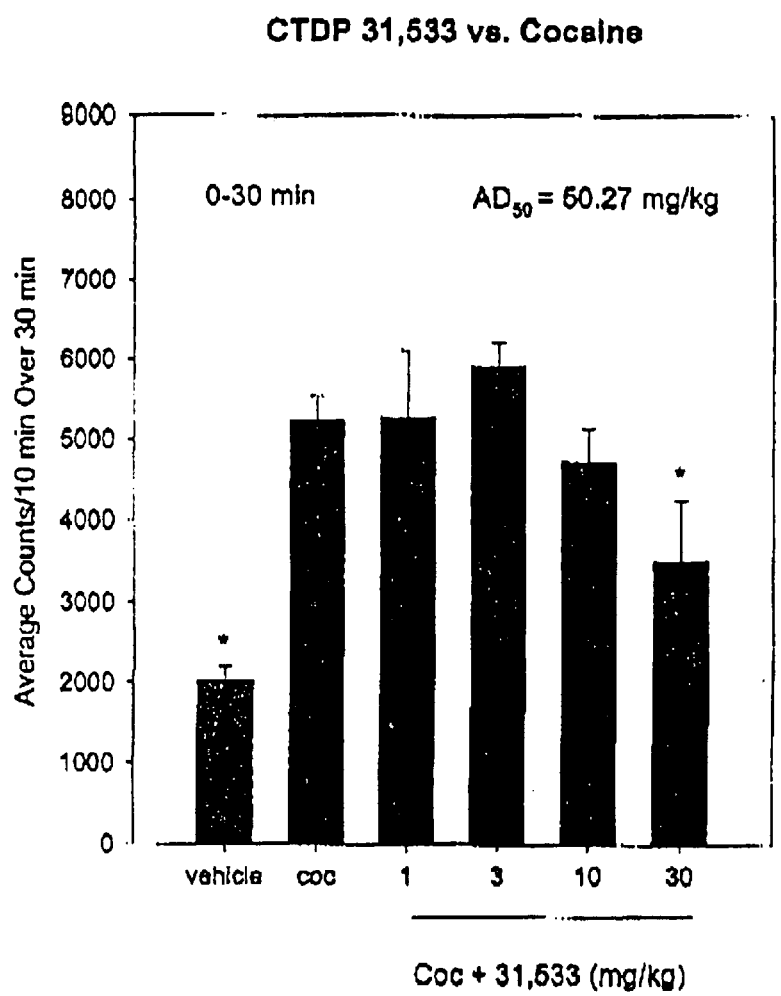
Figure 4 Interaction between 31,533 and cocaine on LMA: Dose response during first 30 min following injection.
*$p < 0.05$ compared with cocaine alone

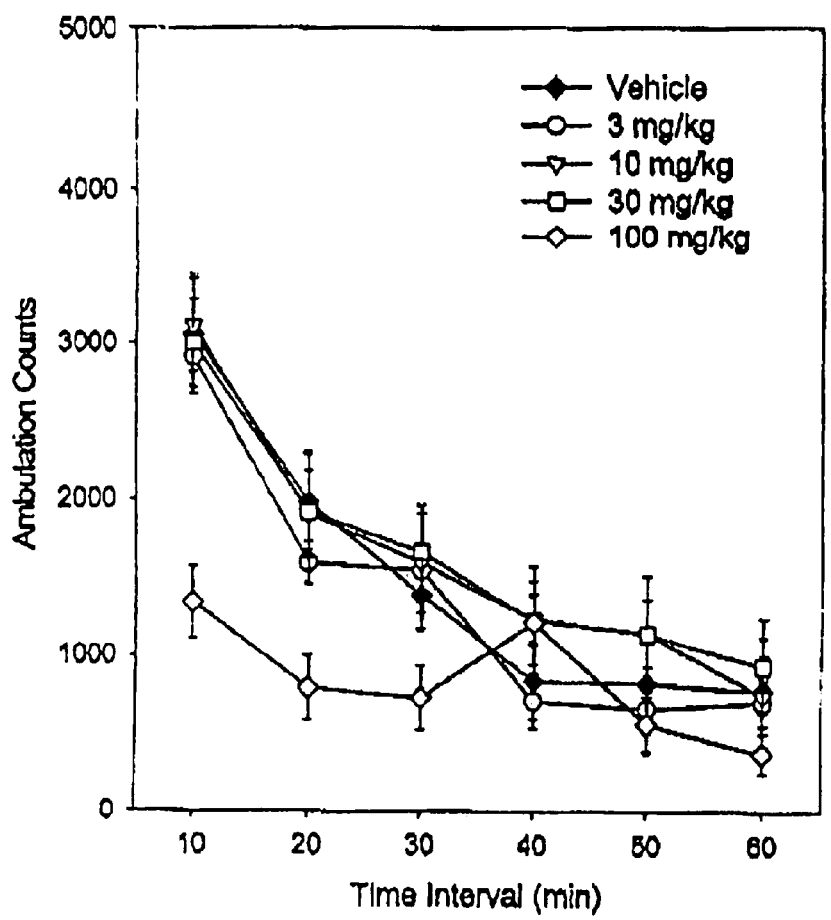
Figure 5 Time course of effects of 31,532 on horizontal activity counts/10 min.

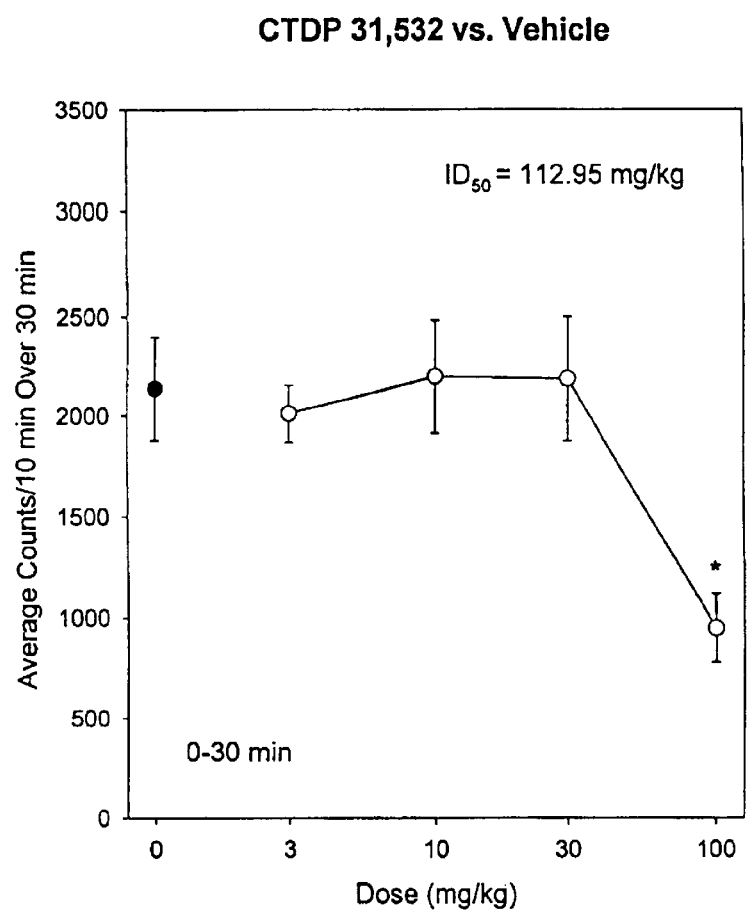
Figure 6 Dose response effects of 31,532 on horizontal activity counts/10 min (0-30 min after 20 min pretreatment).
*$p<0.05$ compared with 0 dose

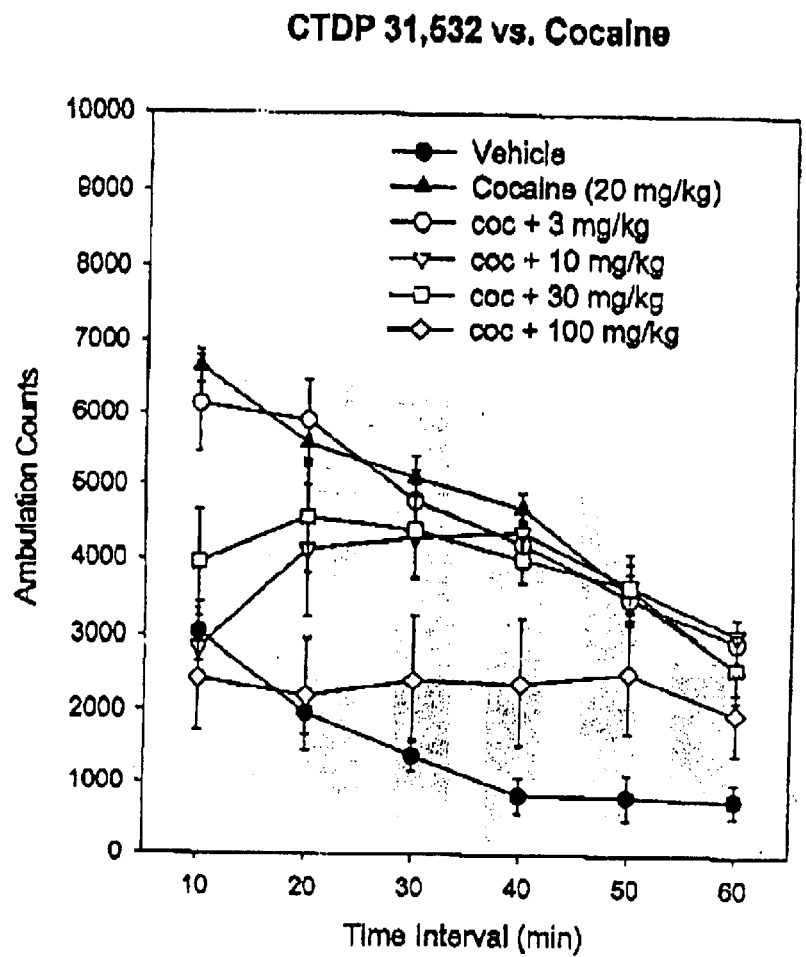
Figure 7 Interaction between 31,532 and cocaine on LMA: Time course of effect.

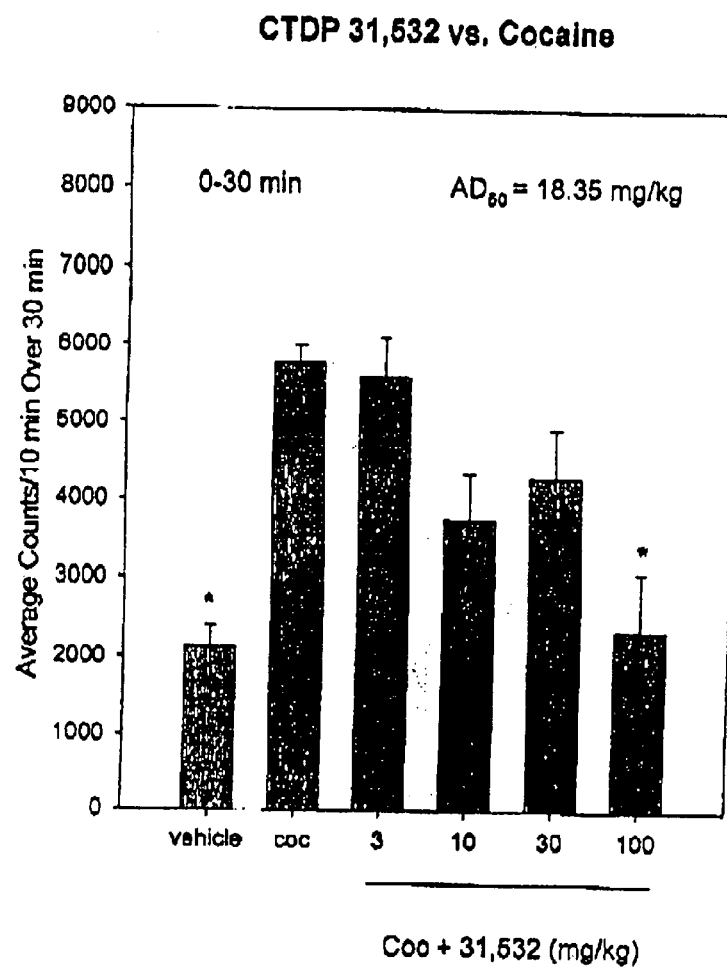
Figure 8 Interaction between 31,532 and cocaine on LMA: Dose response during first 30 min after 20 min pretreatment. *p<0.05 compared with cocaine alone

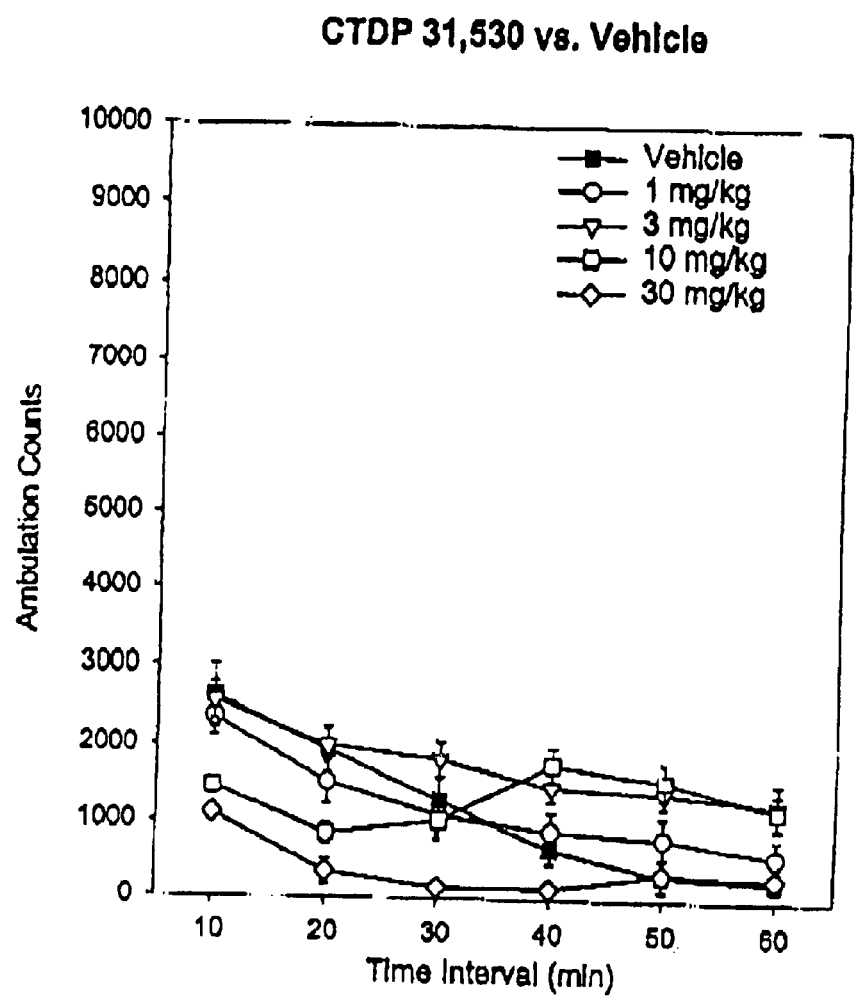
Figure 7 Time course of effects of 31,530 on horizontal activity counts/10 min.
*$p < 0.05$ compared with 0 dose

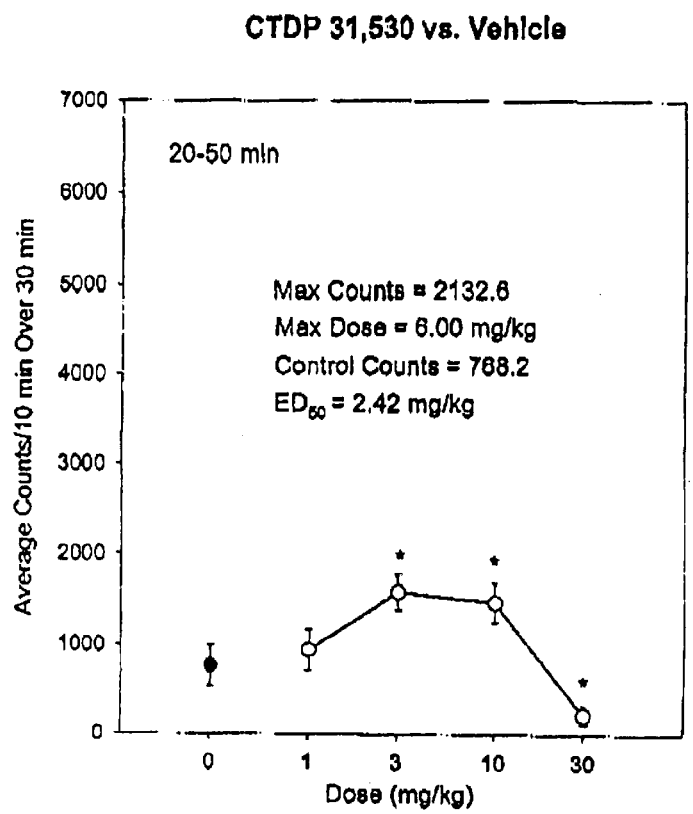
Figure 10 Dose response effects of 31,530 on horizontal activity counts/10 min (20-50 min following injection).
*$p < 0.05$ compared with 0 dose

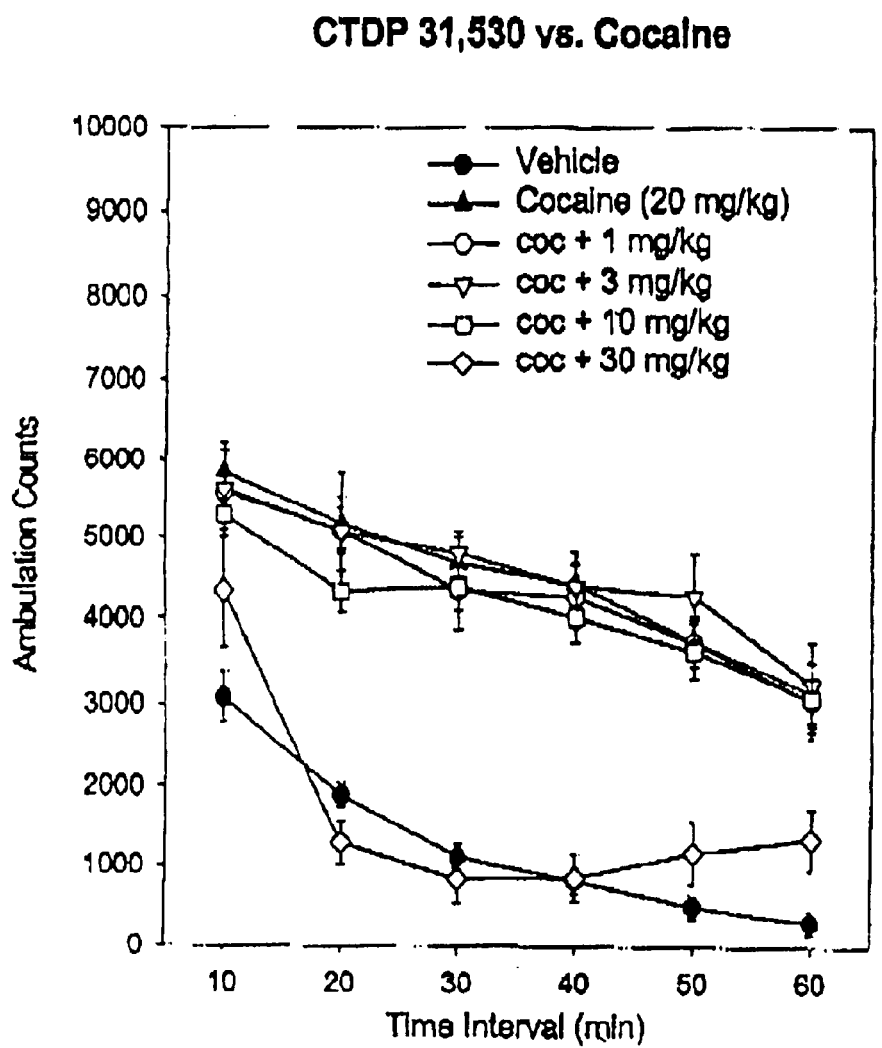
Figure 11 Interaction between 31,530 and cocaine on LMA: Time course of effect.

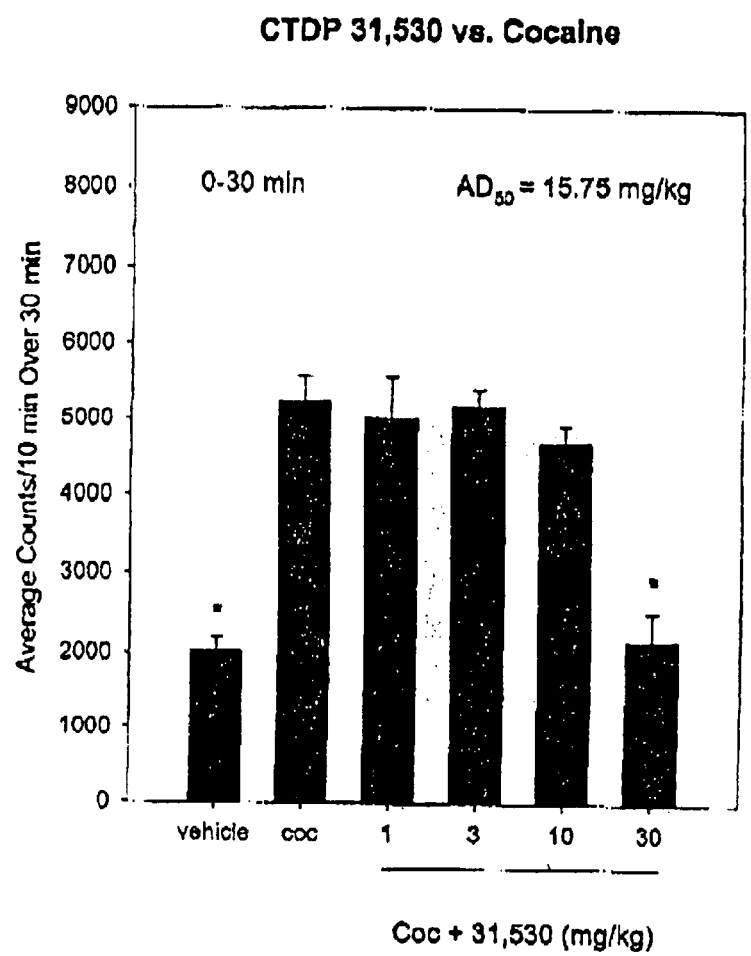
Figure 12 Interaction between 31,530 and cocaine on LMA: Dose response during first 30 min following injection.
*$p < 0.05$ compared with cocaine alone

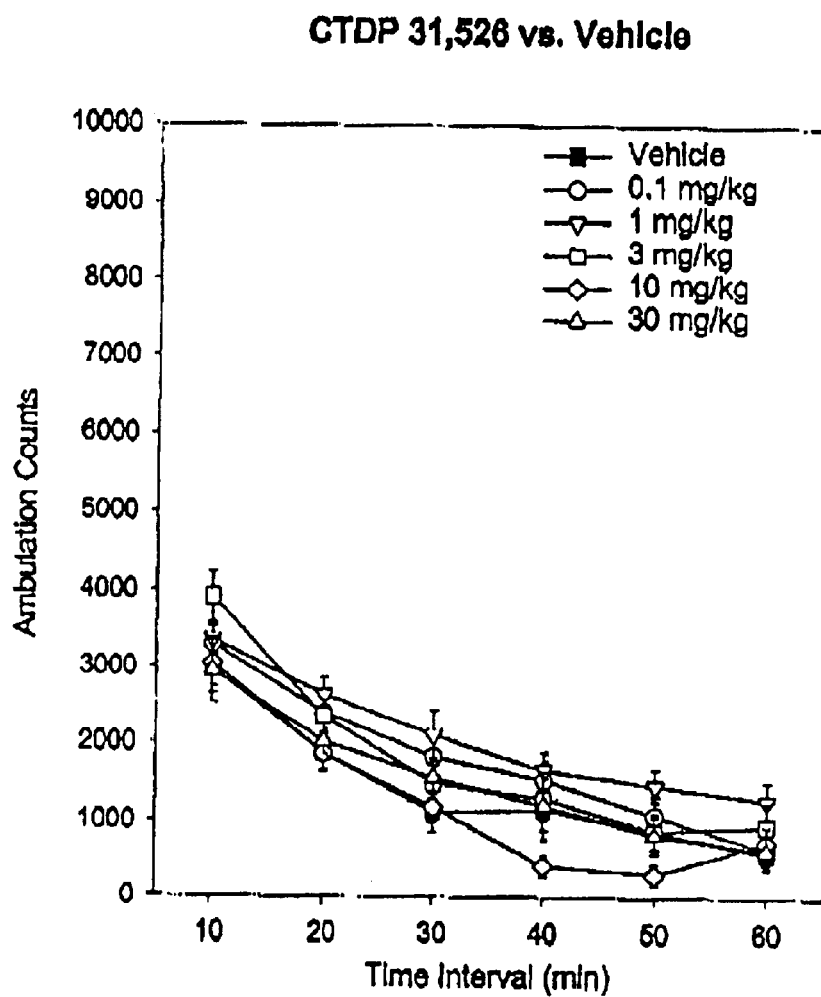
Figure /3Time course of effects of 31,526 on horizontal activity counts/10 min.

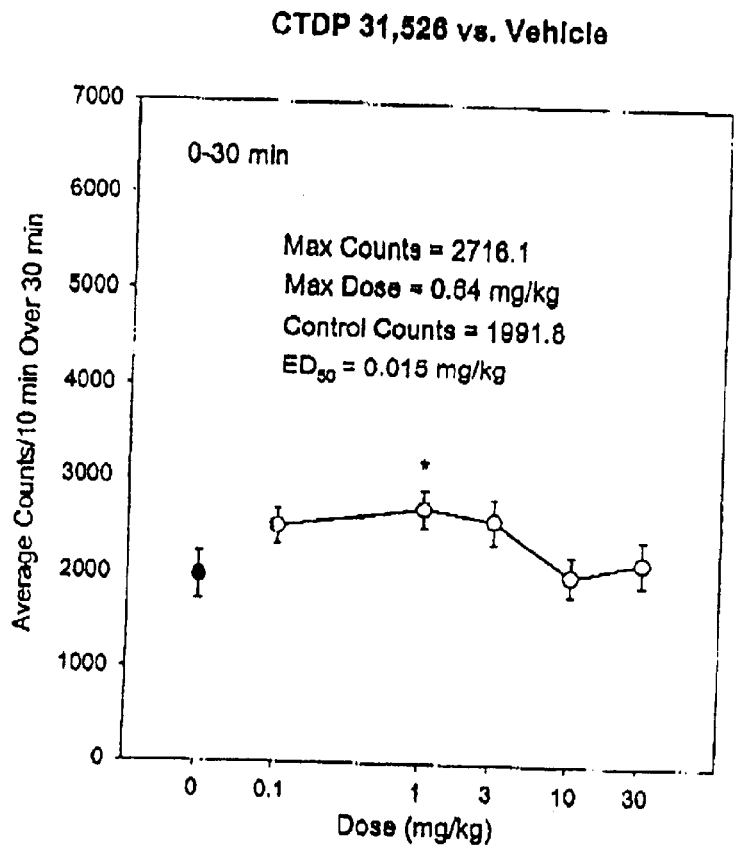
Figure 14 Dose response effects of 31,526 on horizontal activity counts/10 min (0-30 min after 20 min pretreatment).
*$p < 0.05$ compared with 0 dose

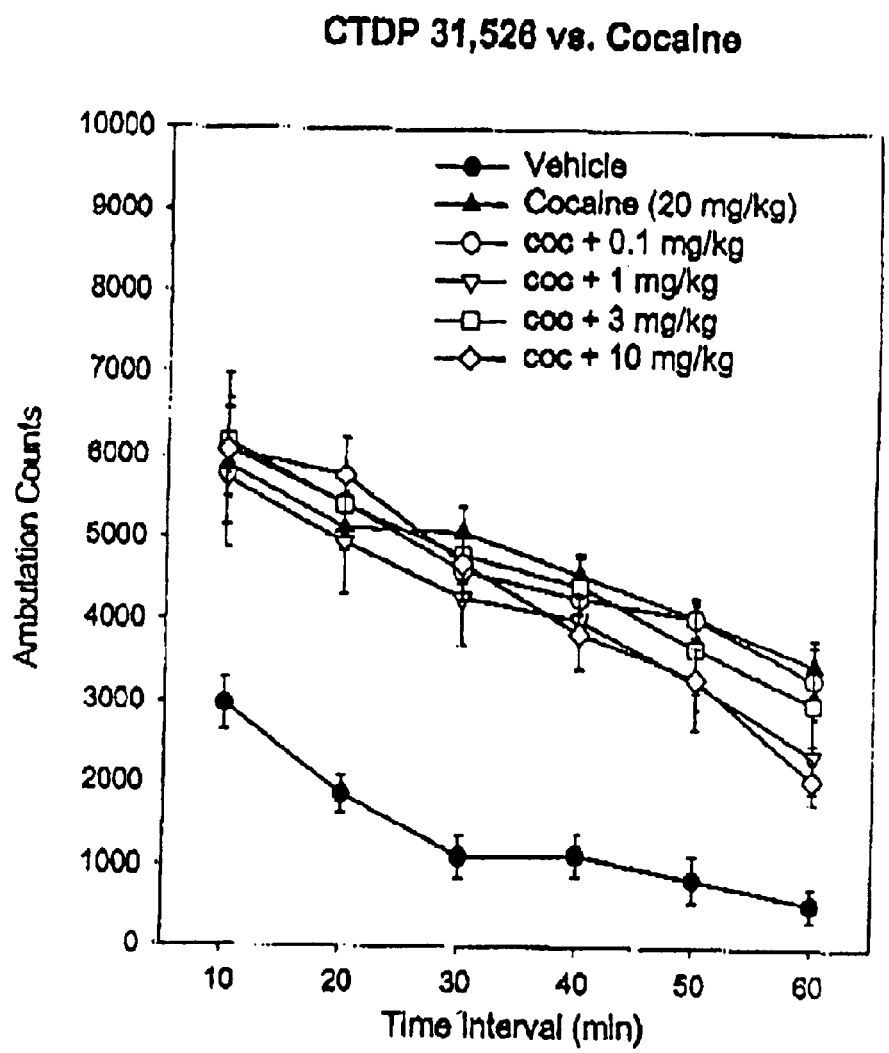
Figure 15 Interaction between 31,526 and cocaine on LMA: Time course of effect.

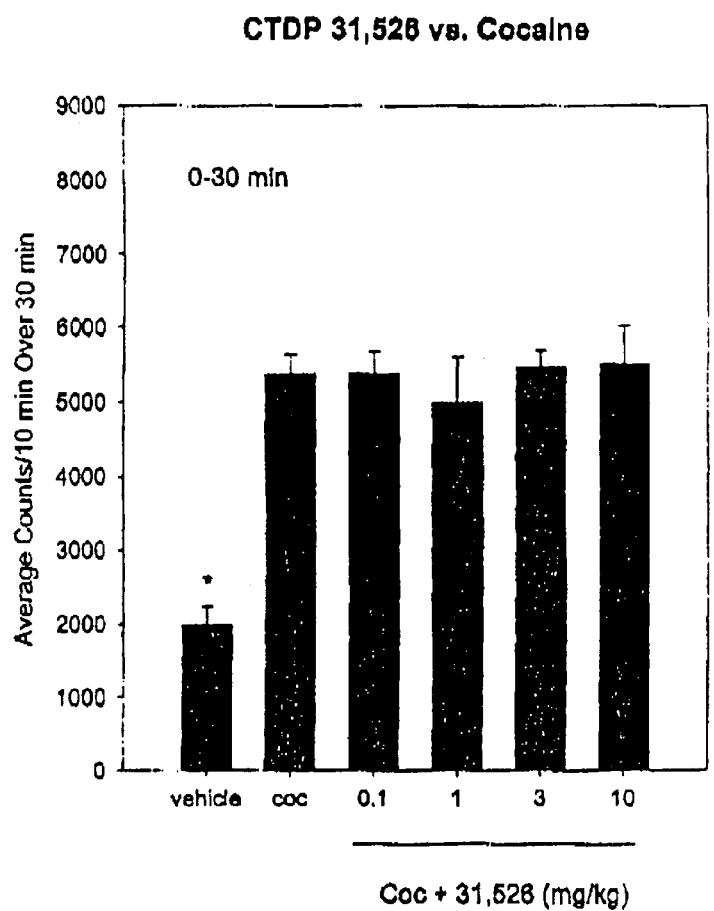
Figure 16 Interaction between 31,526 and cocaine on LMA: Dose response during first 30 min after 20 min pretreatment.
*$p < 0.05$ compared with cocaine alone

Scheme 1
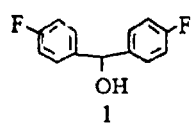 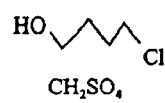 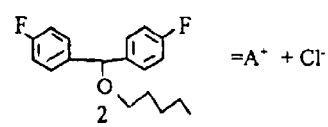
1
2
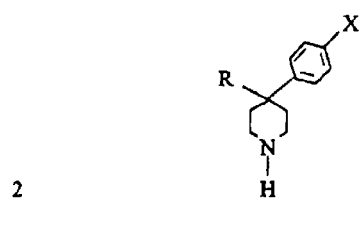
K$_2$CO$_3$/KI
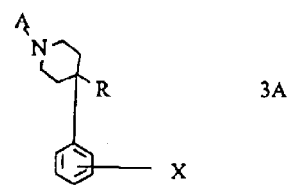
3A
| 3 R = COCH$_3$ | X = H | 31525 |
| 4 R = OH | X = 4 Br | 31530 |
| 5 R = OH | X = H | 31531 |
2
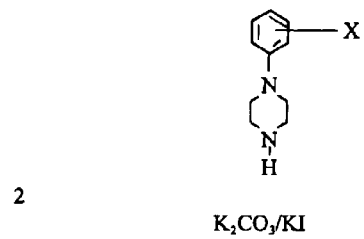
K$_2$CO$_3$/KI
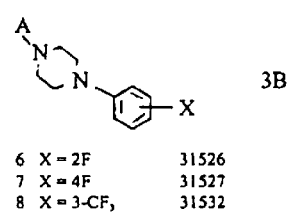
3B
| 6 X = 2F | 31526 |
| 7 X = 4F | 31527 |
| 8 X = 3-CF$_3$ | 31532 |
2
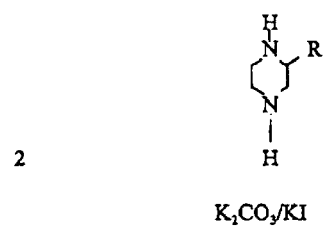
K$_2$CO$_3$/KI
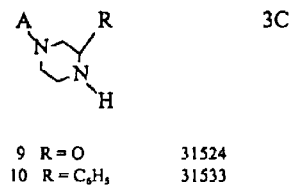
3C
| 9 R = O | 31524 |
| 10 R = C$_6$H$_5$ | 31533 |
Figure 17

DIAGNOSTIC AND THERAPEUTIC PIPERAZINE AND PIPERIDINE COMPOUNDS AND PROCESS

REFERENCE TO RELATED APPLICATIONS

This application is a continuation-in-part of application Ser. No. 09/431,059, filed Nov. 1, 1999 now U.S. Pat. No. 6,251,363 which, in turn is a divisional application of application Ser. No. 08/928,246, filed Sep. 12, 1997 now U.S. Pat. No. 6,001,330.

BACKGROUND OF THE INVENTION

1. Field of the Invention

This invention relates to a diagnostic and therapeutic 1-[2-(diarylmethoxy) alkyl]-4-(3-aryalkyl) piperazines and piperidines, their use as diagnostic or therapeutic agents and to a process for making the piperazines and piperidines.

2. Description of Prior Art

The dopaminergic (DA) neurotransmitter systems are intimately involved with a number of central nervous system (CNS) disorders including those involved with movement, e.g., Parkinson's Disease and reinforcing effects, e.g., cocaine dependency. Interest in these two disorders in particular has stimulated research efforts to develop specific agents that can be used either diagnostically, to evaluate the extent of the disease, or therapeutically to antagonize the effect of cocaine. Cocaine recognition sites are localized on dopamine nerve terminals. Drugs that bind, affect or block these sites therefore have potential uses which include: (i) imaging probes for neurodegenerative disorders; and (ii) imaging probes for dopamine transporter/cocaine binding sites. Furthermore, in many instances these compounds or analogs become active on other sites that affect the serotonergic system and, therefore, may be used to treat disorders associated with serotonin (e.g., depression, PMS, weight, psychosis or aging).

Because of the unique anatomical location of the cocaine recognition sites, a high affinity probe for imaging of these sites in vivo in the brain can be carried out using positron emission tomography (PET) or single photon emission computed tomography (SPECT) imaging. Such imaging is useful for diagnosing or monitoring the Parkinson's disease, other neurological disorders characterized by the degeneration of dopamine nerve terminals or by aging. Preferably, the common target for compounds that would fulfill these objectives is the dopamine transporter (DAT), a 12-transmembrane spanning presynaptic protein that removes the dopamine from the synaptic clef following its release. The two classes of competitive drugs that have been most extensively examined are the stable tropane analogs of cocaine characterized by WIN 35,428 (also known as CFT) and the piperazine derivatives characterized by GBR-12935. Both exert their effect at nanomolar concentrations.

The cocaine analog, 2β-carbomethoxy-3β-(4-fluorophenyl) tropane (CFT) and other analogs have proven to be an effective probe for studying dopamine-related diseases and cocaine binding sites in the striatum. For example, the progression of Parkinson's disease in primate models and subjects can be monitored by administering radiolabeled analogs of CFT and imaging the distribution of radioactivity in the brain. PET has been used to image $^{11}C$ labeled analogs of CFT in primate models, Hantraye et al., Neuroreport 3.265 (1992), Farde et al., Synapse 16:93 (1994) while SPECT has been used to image iodinated CFT analogs in both primate models and human subjects (Shaya et al., Synapse 10:169 (1992) and Neumeyer et al., J. Med. Chem. 34:3144 (1991, Elmaleh et al., J. Nucl. Med.

Various substances (particularly cocaine and cocaine congeners) are potent inhibitors of dopamine transport in the striatum of the brain because they bind to the dopamine transporter. These substances have different affinities or $IC_{50}$'s for inhibiting dopamine transport and for blocking cocaine. The more strongly these substances block dopamine transport, the more strongly they bind to sites on the dopamine transporter which have been labeled by $[^3H]$ cocaine or by $[^3H]$ CFT, Madras et al., (1089) *J. Pharmacol. Exp. Ther.* 251:131–141; and Madras et al. (1989) *Mol. Pharmacol.* 36:518–524. The hope that these compounds might be Parkinson's markers is further supported by the parallel between loss of binding and loss of dopamine in the diseased brain (Madras et al., *Catechol. Symp.* 193, 1992).

Because of its widespread, low cost and simplicity, SPECT is preferred to PET for routine imaging directed towards diagnosis. Technetium-99m is the tracer of choice for SPECT imaging because of its excellent physical characteristics and widespread availability. Recently, technetium-99m CFT analogs were reported which appear to be extracted by the brain and concentrate preferentially in its dopamine rich regions (Madras et al., Synapse 22:239 (1996) and Meegalla et al., J. Am. Chem. Soc. 117:11037 (1995).

There is need for improved diagnostic agents and markers of neurogenerative disorders which have improved specificity for concentrating in dopamine rich regions in the brain. Such agents can provide improved diagnosis for excluding at an early stage of Parkinson's disease as the cause of symptoms which may be useful information in diagnosing other conditions. Moreover, early diagnosis of Parkinson's disease can facilitate the introduction of putative prophylactic drug therapy (e.g., deprenyl) prior to the onset of more severe symptoms, Kaufman and Madras (1991) Synapse 9:43–49. Detection of nerve cell depletion in the presymptomatic phase in an animal model of Parkinson's disease would also be useful, e.g., when using the model to evaluate therapies for Parkinson's disease, Hantraye et al. (1992) Neurol. Reports 3:26–268; and Hahtraye et al. (1992) *Soc. Neurosci. Abstra.* 18:935.

There is a particular need for diagnostic agents and markers of neurogenerative disorders that selectively target a domain transporting protein (the dopamine transporter) in preference to another protein known as the serotonin transporter. In normal brain tissue, the dopamine: serotonin transporter density ratio is approximately 10:1. Diagnostic agents can be used to monitor the effects of Parkinson's disease therapy by determining the loss or reduction of loss of dopamine. In certain neurodegenerative disorders, such as Parkinson's disease, nerve cells that produce dopamine (and on which the dopamine transporter is located) undergo severe depletion while serotonin transporter ratio can fall to 50% in Parkinson's disease.

Accordingly, it would be desirable to provide improved diagnostic and therapeutic compositions which have improved selectivity for being concentrated in dopamine regions of the brain as compared to presently available diagnostic and therapeutic compositions. Such improved diagnostic and therapeutic compositions can provide a means for earlier detecting an abnormal condition of the brain measurable by determining the state of the dopamine rich regions. In addition, such improved therapeutic composition can provide a basis for more effective treatment of a patient such as a cocaine-dependent patient. In addition it is desirable to provide a drug that blocks cocaine uptake while allowing dopamine reuptake. Furthermore, drugs which are partial agonists or antagonists can have a useful application.

SUMMARY OF THE INVENTION

The present invention is based on the discovery that N-[2-bis[arylmethoxy) alkyl piperazines and piperidines have high affinity and high selectivity for dopamine transporters.

The compounds of this invention are represented by the Formula I and physiologically acceptable salts thereof:

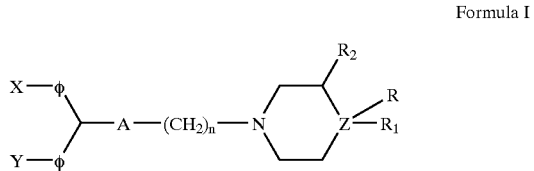

Formula I wherein:
A is oxygen or nitrogen; n is an integer of 2 to 6; X and Y can be the same or different and are hydrogen, halogen, nitro, alkyl or halalkyl, Z is carbon or nitrogen; and φ is phenyl, naphthyl, thienyl or pyridinyl.

When Z is carbon, R is hydrogen, cyano, hydroxy, —COOCH$_3$, —CH$_2$OH or —COOH; R$_1$ is 4-fluorophenyl, 4-chlorophenyl, 4-trifluoromethyl-3-chlorophenyl, 4-bromophenyl, 4-(2-keto-1-benzimidazolinyl) or 1-phenyl-1, 3, 8-triazaspiro [4,5] decan-4-one. When Z is nitrogen, R and R$_1$ combined are

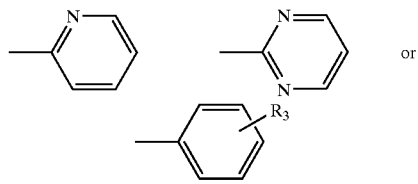 or

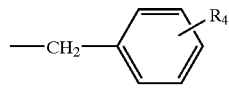

wherein R$_3$ is halo, alkyl, cyano or nitro and R$_2$ can be hydrogen or

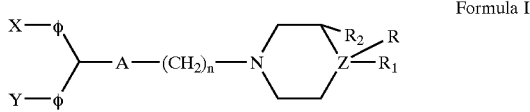

wherein R$_4$ is halo, alkyl, cyano, nitro, alkylnyl or alkenyl.

The compounds of this invention are useful as diagnostic agents in their labeled form with radionuclides such as $^{123}$I, $^{125}$I, $^{99m}$Tc or the like. In their labeled or unlabeled form, the compounds of this invention are useful as therapeutic acceptable carrier. Such compositions can be used to selectively image cocaine binding regions of the central nervous system of a human patient by administering detectably labeled compound of this invention to the central nervous system and detecting the binding of that compound to CNS tissue by (PET) or (SPECT). Such a compound also are useful in treatment of neurodegenerative disorders characterized by dopamine deficits or cocaine abuse and to follow the effects of therapy for dopamine or cocaine abuse.

BRIEF DESCRIPTION OF THE DRAWINGS

FIG. 1 shows the average horizontal activity counts as a function of time in Example 9.

FIG. 2 shows the average horizontal activity counts as a function of dose in Example 9.

FIG. 3 shows the average horizontal activity counts as a function of time in Example 10.

FIG. 4 shows the average horizontal activity counts as a function of dose in Example 10.

FIG. 5 shows the average horizontal activity counts as a function of time in Example 11.

FIG. 6 shows the average horizontal activity counts as a function of dose in Example 11.

FIG. 7 shows the average horizontal activity counts as a function of time in Example 12.

FIG. 8 shows the average horizontal activity counts as a function of dose in Example 12.

FIG. 9 shows the average horizontal activity counts as a function of time in Example 13.

FIG. 10 shows the average horizontal activity counts as a function of dose in Example 13.

FIG. 11 shows the average horizontal activity counts as a function of time in Example 14.

FIG. 12 shows the average horizontal activity counts as a function of dose in Example 14.

FIG. 13 shows the average horizontal activity counts as a function of time in Example 15.

FIG. 14 shows the average horizontal activity counts as a function of dose in Example 15.

FIG. 15 shows the average horizontal activity counts as a function of time in Example 16.

FIG. 16 shows the average horizontal activity counts as a function of dose in Example 17.

FIG. 17 is a schematic diagram illustrating the process for producing the compounds of this invention.

DESCRIPTION OF SPECIFIC EMBODIMENTS

The piperazine and piperidine compounds of this invention are prepared for administration to an animal in the form of a pharmaceutically acceptable free base or a salt such as tartrate, citrate, napthalene-1.5-disulfonate, fumarate, maleate, hydrochloride or hydrobromide salts.

The compounds of this invention are represented by the Formula I and physiologically acceptable salts thereof

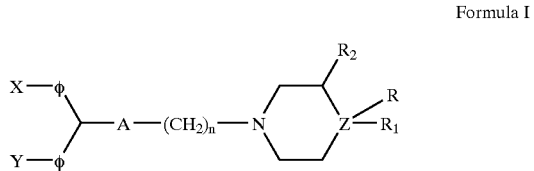

Formula I wherein: A is oxygen or nitrogen; n is an integer of 2 to 6; X and Y can be the same or different and are hydrogen, halogen, nitro, alkyl or halalkyl, Z is carbon or nitrogen; and φ is phenyl, naphthyl, thienyl or pyridinyl.

When Z is carbon, R is hydrogen, cyano, hydroxy, —COOCH$_3$, —CH$_2$OH or —COOH; R$_1$ is 4-flurophenyl, 4-chlorophenyl, 4-trifluoromethyl-3-chlorophenyl, 4-bromophenyl, 4-(2-keto-1-benzimidazolinyl) or 1-phenyl 1, 3, 8-triazaspiro [4,5]decan-4-one. When Z is nitrogen, R and R$_1$ combined are

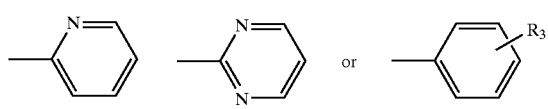

wherein $R_3$ is halo, alkyl, cyano or nitro and $R_2$ can be hydrogen or

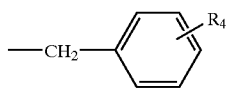

wherein $R_4$ is halo, alkyl, cyano, nitro, alkylnyl or alkenyl.

The preferred compounds of this invention are characterized by the formula:

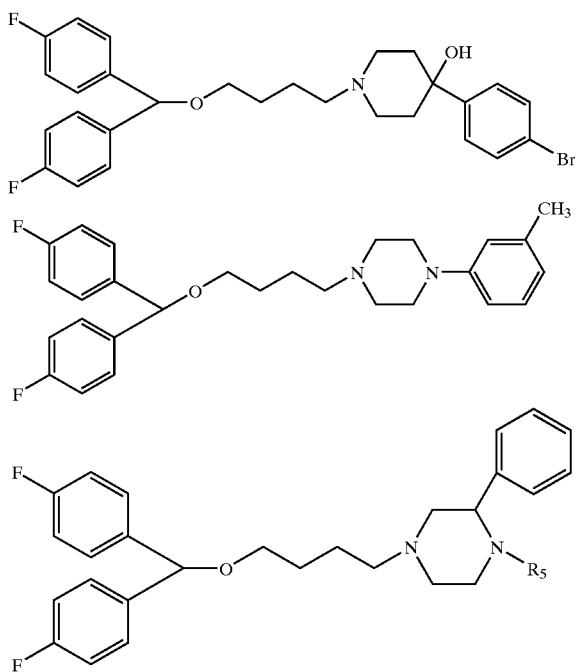

in the R, S, or R,S form
wherein $R_5$ is hydrogen halo, alkyl, cyano or nitro.

The compounds of this invention can be labeled with a radionuclide by any conventional process such as when $^{123}$I or $^{125}$I which are bound to the compound at the X or Y position or with $^{99m}$Tc which is bound to the compound at the X or Y position or with a derivitized nitrogen such as in the positions of $R_1$, $R_2$ or $R_3$.

The piperazine and piperidine compounds of this invention are useful for imaging organs containing dopamine receptors in an animal including humans. The piperazine and piperidine compounds of this invention are particularly useful for imaging dopamine neurons in the brain, for example detecting the loss of dopamine neurons in the brain. The piperazine and piperidine compounds of this invention bind the dopamine transporter with higher affinity than currently used dopamine imaging agents. In addition, the piperazine and piperidine compounds are selective for the dopamine transporter and have good distribution to and penetration of the brain. Therefore, utilization of the piperazine and piperidine compounds may enable earlier diagnosis of neurogenerative disorders than is now possible as well as the monitoring of the effectiveness of the treatment.

Imaging dopamine neurons in the brain with the compounds of this invention is used for monitoring the brain uptake of drugs such as cocaine or cocaine substitutes. The compounds of this invention may block cocaine binding but permit reuptake of dopamine. The craving experienced by individuals who abuse cocaine is a result of the occupancy of the dopamine transporter by the drug. Cocaine abuse can be treated with drugs that occupy the sites associated with the dopamine transporter in place of dopamine or cocaine. Imaging of the dopamine neurons in the brain with piperazine and piperidine compounds of the invention is used to identify drugs which occupy the sites or other site of cocaine uptake and therefore have potential to treat individuals who abuse cocaine. In many instances the analog may preferably occupy sites associated with seratonin.

The dopamine neurons in an individual can be imaged by administering an imaging dose of one of the radiolabeled piperazine and piperidine compounds, for example, a piperazine and piperidine derivative represented by structural Formula II. An "imaging dose" of a piperazine and piperidine compound is an amount which concentrates in an organ with dopamine neurons and which has sufficient radioactivity so that the distribution of dopamine neurons in the organ can be converted into an image by a technique such as PET or SPECT. An "imaging dose" of the piperazine and piperidine compound of the diamine compound of this invention typically ranges from about 0.5 mCi to about 50 mCi and with a specific activity ranging from about 1 mCi/$\mu$M to about 100 mCi/$\mu$M, preferably from about 1 mCi to about 20 mCi and with a specific activity ranging from about 10 Ci/$\mu$M to about 100 Ci/$\mu$M, but will vary according to factors such as the general health, age and sex of the individual and the particular application.

In one aspect of this invention, a method of treating a subject is provided in which a desirable therapeutic effect can be achieved by occupying the dopamine transporter receptor with an agent or drug. Suitable subjects include individuals with Parkinson's disease, brain aging, Huntington's disease, tardive dyskinesiaa and schizophrenia. The method comprises administering to the subject a therapeutically effective amount of this invention with a pharmaceutically acceptable carrier. A "therapeutically effective amount" is the amount which brings about the amelioration of symptoms or slows the progression of one of the above-monitored conditions. Suitable dosages range from about 0.01 mg/kg per day to about 100 mg/kg per day. In another aspect some of these compounds show selectivity to the sertonin transporter and/or mixed activity for both dopamine and serotonin and therefore, are useful for treating disorders associated with serotonin.

The piperazine and piperidine compounds are generally administered intravenously when used for imaging dopamine neurons. An appropriate composition comprising the compound to be administered can be prepared in a physiologically acceptable vehicle or carrier. Suitable carriers include, for example, a dermal patch, aqueous or alcoholic/aqueous solutions, saline and buffered media. Intravenous vehicles can include various additives, preservatives, or fluid nutrients or electrolyte replenishers (See, generally, *Remington's Pharmaceutical Science,* 161 Edition, Mack, Ed. (1990).

When used for treatment, the piperazine and piperidine compounds of this invention can be administered by a variety of known methods, including orally or by parenteral routes (e.g., intramuscular, intravenous, transdermal, subcutaneous, nasal or topical). The form in which the compounds are administered will be determined by the route of administration. Such forms will include, but are not limited to capsular and tablet formulations (for oral administration), liquid formulations (for oral, intravenous, intramuscular or subcutaneous administration) and slow releasing micro carriers (for intramuscular or intravenous administration). The formulations can also contain a physiologically acceptable vehicle and optional adjuvants, flavorings, colorants and preservatives. Suitable physiologically acceptable vehicles may include saline, sterile water, Ringer's solution, and isotonic sodium chloride solutions. Autoradiographic distribution of the compounds are conducted according to in vitro techniques (Kaufman et al., *Synapse* 9:177 (1991) or ex vivo techniques (Kaufman and Madras, *Synapse* 12:99 (1992)). SPECT or PET imaging may be carried out using any appropriate apparatus. Imaging is carried out on conscious subject using standard imaging (see, e.g., *Medicine, Scientific American, Inc.*, ed. Rubenstein and Federman, 1988; Jaszczak and Coleman, Invest. Radio. 20:897 (1985); and Coleman et al., *Invest. Radiol.* 21:1 (1986)).

The piperazine and piperidine compounds of this invention can be prepared as indicated in Scheme 1. Modifications to these syntheses to prepare compounds other than those specifically depicted can be carried out by one or ordinary skill in the art using no more than routine experimentation.

EXAMPLE 1

The synthetic scheme for the preparation of representative N-(bisarylmethoxy) alkyl-$N_1$ or N-(bisarylmethoxy) butyl piperidines of this invention is depicted in Scheme 1. The requisite starting materials were prepared according to the procedures of J. Med. Chem., 1999, 42:3647–3656 which is incorporated herein by reference. Compound 2 was made by reacting conc. $H_2SO_4$ with 4,4'-difluorobenzhydrol with 1-hydroxy-4-chloro butene in toluene for 24 hours at 80–90° C. The reaction mixture was cooled and washed with saturated $NaHCO_3$ and saturated NaCl. Compounds 3, 4 and 5 were prepared from compound 2 by alkylation as disclosed by the J. Med. Chem references. Compounds 6, 7 and 8 were prepared by the same alkylation. Compounds 9 and 10 were prepared by the same alkylation.

Biological Evaluation Method

The requisite starting materials also were prepared according to the procedures of J. Med. Chem., 1999, 42:3647–3656.

By NIDA/MDD (NIDA contract NOIDA-7-8071, Contract Title: *In Votro* Biogenic Amine Transporter Testing for potential cocaine treatment medication". Published method by Eshleman et al. J. Pharmacol. Exp. Ther. 1999, 289:877–885 provided by Aaron Janowsky, Ph.D. Oregon Health Sciences University, Portland, Oreg. Biological evaluation of these compounds was carried out in HEK 293 cells expressing cDNA for human domapine transposrter (hDAT), human serotonin transporter (hSERT) and human norepinephrine transporter (hNET). All compounds were tested for their displacement of [$^{125}$I] RTI and their ability to inhibit uptake of [$^3$H]DA, [$^3$H]5-HT and [$^3$H]NE. The in vitro results of the biological assays were shown in Table 1 and 2. Drugs (10 mM stock solution) are dissolved in DMSO. The final DMSO concentration in the assay is 0.01 percent. Pipetting is performed with a Biomek 2000 robotic work station.

[$I^{125}$] RTI-55 Binding;

Preparation: Cells are grown on 150 mm diameter tissue culture dishes. Medium is poured off the plate, the plate is washed with 10 ml of phosphate buffered saline, and 10 ml of lysis buffer (2 mM HEPES, 1 mM EDTA) are added. After 10 min, cells are scraped from plates and poured into centrifuge tubes and centrifuged for 20 min at 30,000×g. Supernatant is removed, and the pellet is resuspended in 20–32 ml 0.32 M sucrose, depending on the density of binding sites in a given cell line (i.e., a resuspension volume which results in binding $\leq 10\%$ of the total radioactivity), with a Polytron at setting 7 for 10 sec. Assay: Each assay contains 50 $\mu$l membrane preparation (approximately 15 $\mu$g protein), 25 $\mu$l of drug, and 25 $\mu$l of [$^{125}$I] RTI-55 (40–80 pM final concentration) in a final volume of 250 $\mu$l. Krebs HEPES is used for all assays. Membranes are preincubated with drugs for 10 min prior to addition of [$^{125}$I] RTI-55. The reaction is incubated for 90 min at room temperature in the dark and is terminated by filtration onto GF/C filters using a Tom-tech harvester. Scintillation fluid is added to each square and radioactivity remaining on the filter is determined using a Wallac $\mu$-or $\beta$-plate reader. Competition experiments are conducted with duplicate determinations. Data is analyzed using GraphPAD Prism, with $IC_{50}$ values converted to $K_1$ values using the Cheng-Prusoff equation.

$^3$H] Neurotransmitter Uptake for 11EK 293 Cells Expressing Recombinant Amine Transporters:

Filtration Assay:

Preparation: Cells are plated on 150 mm dishes and grown until confluent. The medium is removed, and cells are washed twice with room temperature phosphate buffered saline (PBS). Following addition of PBS (3 ml), the plates are placed in a 25° C. water bath for 5 min. The cells are gently scraped then triturated with a pipette. Cells from multiple plates are combined. One plate provides enough cells for 48 wells, which test two drug curves. Assay: The assay is conducted in 96 1 ml vials and uses the Tomtech Harvester and Betaplate reader. Krebs HEPES (350 $\mu$l) and drugs (50 $\mu$l) are added to vials and placed in a 25° C. water bath. Cells (50 $\mu$l) are added, preincubated for 10 min. and [$^3$H]DA, [$^3$H]5HT or [$^3$H]NE (50 $\mu$l, 20 nM final concentration) is added. Uptake is terminated after 10 min. by filtration on the Tomtech Harvester using filters presoaked in 0.05% polyethyleneimine. Assays are conducted in triplicate with 6 drug concentrations. Data is analyzed using GraphPAD Prism. Provided by Aaron Janowsky, Ph.D. Oregon Health Sciences University, Portland, Oreg.

TABLE 1

Binding Affinities at the DA, 5-HT and NE Transporters, Labeled with [$^{125}$I] RTI-55 of N-Butylpiperidine GBR-type Analogs (Ki ± SD, NM).[a]

| | | | Binding | | | discrimination ratios | |
|---|---|---|---|---|---|---|---|
| Compound | R | X | DAT | SERT | NET | SERT/DAT | NET/DAT |
| 31524 | =O | | 4100 ± 790 | 1800 ± 450 | >10 $\mu$M | 0.4 | >2.4 |
| 31525 | —COCH$_3$ | H | 21.7 ± 8.0 | 126 ± 45 | 114 ± 4.1 | 5.8 | 5.3 |

TABLE 1-continued

Binding Affinities at the DA, 5-HT and NE Transporters, Labeled with [$^{125}$I] RTI-55 of N-Butylpiperidine GBR-type Analogs (Ki ± SD, NM).[a]

| Compound | R | X | Binding | | | discrimination ratios | |
|---|---|---|---|---|---|---|---|
| | | | DAT | SERT | NET | SERT/DAT | NET/DAT |
| 31526[b] | | 2-F | 38.7 ± 5.6 | 30.0 ± 8.4 | 417 ± 34 | 0.8 | 10.8 |
| 31527 | | 4-F | 26.5 ± 3.0 | 34 ± 12 | 207 ± 20 | 1.3 | 7.8 |
| 31530 | —OH | 4-Br | 3.9 ± 1.8 | 38 ± 10 | 250 ± 110 | 9.7 | 64.1 |
| 31531 | —OH | H | 6.4 ± 1.2 | 17.9 ± 8.8 | 54 ± 16 | 2.8 | 8.4 |
| 31532 | | 3-CF$_3$ | 32.5 ± 4.1 | 222 ± 80 | 221.6 ± 9.7 | 6.8 | 6.8 |
| 31533 | —C$_6$H$_5$ | | 3.81 ± 0.84 | 74.6 ± 5.8 | 190 ± 50 | 19.6 | 49.9 |
| cocaine | | | 271 ± 65 | 217 ± 23 | 1730 ± 280 | | |

[a]The Ki values of the test agents were determined in the above assays as described in previous section
[b]as shown in bold tested for in vivo locomotor activity The results in Table I show that most of the new compounds demonstrate the ability to inhibit dopamine uptake at concentrations comparable to or lower than that reported for cocaine. Compounds 31,533 and 31,530 which possessed the highest affinity, also demonstrated high selectivity for the dopamine transporter (10 nM) as compared to norepinephrine (>10,000 nM) or serotonin (1500 nM) transporters.

In summary, this series of analogs of the piperazine containing DAT inhibitors, demonstrates substantial affinity and selectivity for the dopamine transporter.

TABLE 2

DA, 5-HT and NE Reuptake Inhibition and Ratio of Reuptake to Binding (DA) of N-Butylpiperidine GBR-type Analogs (Ki ± SD, nM).[a]

| Compound | R | X | Reuptake | | | Discrimination ratios |
|---|---|---|---|---|---|---|
| | | | [$^3$H]DA | [$^3$H]5-HT | [$^3$H]NE | uptake/binding (DA) |
| 31524 | =O | | 2290 ± 200 | 1800 ± 450 | >10 μM | 0.6 |
| 31525 | —COCH$_3$ | H | 1030 ± 330 | >10 μM | 2550 ± 950 | 47.5 |
| 31526[b] | | 2-F | 460 ± 140 | 192 ± 21 | 700 ± 240 | 11.9 |
| 31527 | | 4-F | 610 ± 150 | 440 ± 50 | 225 ± 28 | 23.0 |
| 31530 | —OH | 4-Br | 431 ± 88 | 3070 ± 830 | 1870 ± 670 | 110.5 |
| 31531 | —OH | H | 96 ± 11 | 136 ± 41 | 179 ± 47 | 15.0 |
| 31532 | | 3-CF$_3$ | 380 ± 130 | 3300 ± 1300 | 310 ± 100 | 11.7 |
| 31533 | —C$_6$H$_5$ | | 550 ± 140 | 700 ± 260 | 290 ± 130 | 144.4 |
| cocaine | | | 278 ± 53 | 189 ± 31 | 209 ± 36 | |

[a]The Ki values of the test agents were determined in the above assays as described in previous section
[b]as shown in bold tested for in vivo locomotor activity

EXAMPLE 2

Compound #31,524 was tested for its effects on radioligand [I$^{125}$] RTI-55) binding to and [$^3$H] dopamine uptake by HEK cells expressing cDNA for the human dopamine transporter (HEK-hDAT cells), its effect on radioligand ([I$^{125}$] RTI-55) binding and [$^3$H) serotonin uptake by HEK cells expressing cDNA for the human serotonin transporter (HEK-hSERT cells), and its effects on radioligand ([I$^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was lower than the affinity of cocaine, the standard compound, for the same site(s). The K$_i$ value for the displacement of [I$^{125}$] RTI-55 by 31,524 was 4100 nM, and the K$_i$ value for cocaine displacement of [I$^{125}$] RTI-55 binding was 271 nM. In the uptake assays 31,524 was less potent at blocking the uptake of [$^3$H] dopamine, with an IC$_{50}$ value of 2290 nM, as compared to the potency of cocaine (IC$_{50}$=278 nM). A Hill coefficient other than one suggests complex interactions with binding or uptake sites.

In HEK-hSERT cells, the affinity of the compound for the binding site was lower than the affinity of cocaine, the standard compound, for the same site(s). The K$_i$ value for the displacement of [I$^{125}$] RTI-55 by 31,524 was 1800 nM and the K$_i$ value for cocaine displacement of [I$^{125}$] RTI-55 binding was 217 nM. In the uptake assays 31,524 was less potent at blocking the uptake of [$^3$H]seratonin, with an IC$_{50}$ value of 5340 nM, as compared to the potency of cocaine (IC$_{50}$=189 nM).

In HEK-hNET cells, the affinity of the compound for the binding site was lower than the affinity of cocaine, the standard compound, for the same site(s). The K$_1$ value for the displacement of [I$^{125}$] RTI-55 by 31,524 was >10 μl and the K$_i$ value for cocaine displacement of [I$^{125}$] RTI-55 binding was 1730 nM. Uptake assays are not conducted if the K$_1$ value is greater than 10 μM.

Effects of 31,524 on HEK-hDAT, HEK-hSERT and HEK-hNET cells

| | 31,524 | Cocaine |
|---|---|---|
| HEK-hDAT cells | | |
| [[I$^{125}$] RTI-55 binding K$_1$(nM) | 4100 ± 790 | 271 ± 65 |
| Hill coefficient | −064 ± 0.03 | −0.591 ± 0.06 |
| [$^3$H] Dopamine Uptake IC$_{50}$ (nM) | 2290 ± 200 | 278 ± 53 |

-continued

Effects of 31,524 on HEK-hDAT, HEK-hSERT and HEK-hNET cells

|  | 31,524 | Cocaine |
|---|---|---|
| HEK-hSERT cells |  |  |
| [[$I^{125}$] RTI-55 binding $K_i$(nM) | 1800 ± 450 | 217 ± 23 |
| Hill coefficient | −0.80 ± 0.09 | −0.85 ± 0.06 |
| [$^3$H] Serotonin Uptake $IC_{50}$ (nM) | 5340 ± 950 | 189 ± 31 |
| HEK-hNET cells |  |  |
| [$^{125}$I] RTI-55 binding $K_i$(nM) | >10 μM | 1730 ± 280 |
| Hill coefficient |  | −0.76 ± 0.05 |
| [$^3$H] NE Uptake $IC_{50}$ (nM) |  | 209 ± 36 |

Numbers represent the means ± SEM from at least three independent experiments, each conducted with duplicate (for binding assays) or triplicate (for uptake assays) determinations. When the $K_i$ or the $IC_{50}$ for the test compound is greater than 10 μM, only two experiments are conducted and no standard error is reported.

EXAMPLE 3

Compound #31,525 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,525 was 21.7 nM, and the $K_i$ value for cocaine displacement of [$I^{125}$] RTI-55 binding was 271 nM. In the uptake assays 31,525 was less potent at blocking the uptake of [$^3$H] dopamine, with an $IC_{50}$ value of 1030 nM, as compared to the potency of cocaine ($IC_{50}$=278 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55 by 31,525 was 126 nM, and the $K_1$ value for cocaine displacement of [$I^{125}$] RTI-55 binding was 217 nM. In the uptake assays, 31,525 was less potent at blocking the uptake of [$^3$H] serotonin, with an $IC_{50}$ value of >10 μM, as compared to the potency of cocaine ($IC_{50}$=189 nM).

In HEK-hNET cells, the affinity of the compound for the binding site was higher than the affinity of cocaine, the standard compound, for the same site(s). The $K_1$ value for the displacement of [$I^{125}$) RTI-55 by 31,525 was 114 nM, and the $K_1$ value for cocaine displacement of [125] RTI-55 binding was 1730 nM. In the uptake assays, 31,525 was less potent at blocking the uptake of [$^3$H] norepinephrine, with an $IC_{50}$ value of 2550 nM; as compared to the potency of cocaine ($IC_{50}$=209 nM).

Effects of 31,525 on HEK-hDAT, HEK-hSERT and HEK-hNET cells

|  | 31,525 | Cocaine |
|---|---|---|
| HEK-hDAT cells |  |  |
| [$I^{125}$] RTI-55 binding $K_i$(nM) | 21.7 ± 80 | 2719 ± 65 |
| Hill coefficient | −0.61 ± 0.01 | −0.59 ± 0.06 |
| [$^3$H] Dopamine Uptake $IC_{50}$ (nM) | 1030 ± 330 | 278 ± 53 |
| HEK-hSERT cells |  |  |
| [$I^{125}$] RTI-55 binding $K_i$(nM) | 126 ± 45 | 217 ± 23 |
| Hill coefficient | −0.75 ± 0.05 | −0.85 ± 0.06 |
| [$^3$H] Serotonin Uptake $IC_{50}$ (nM) | >10 μM | 189 ± 31 |
| HEK-hNET cells |  |  |
| [$I^{125}$] RTI-55 binding $K_i$(nM) | 114 ± 41 | 1730 ± 280 |
| Hill coefficient | −0.71 ± 0.06 | −0.76 ± 0.05 |
| [$^3$H] NE Uptake $IC_{50}$ (nM) | 2550 ± 950 | 209 ± 36 |

Numbers represent the means ± SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

EXAMPLE 4

Compound #31,526 was tested for its effects on radioligand [$I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 526 was 38.7 nM, and the $K_i$ value for cocaine displacement of [$I^{125}$] RTI-55 binding was 271 nM. In the uptake assays 31,526 had about the same potency at blocking the uptake of [$^3$H] dopamine, with an $IC_{50}$ value of 460 nM, as compared to the potency of cocaine ($IC_{50}$=278 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_i$ value for the displacement of [$I^{125}$] RTI-55 by 31,526 was 30.0 nM, and the $K_1$ value for cocaine displacement of [$I^{125}$] RTI-55 binding was 217 nM. In the uptake assays, 31,526 had about the same potency at blocking the uptake of [$^3$H] serotonin, with an $IC_{50}$ value of 192 nM, as compared to the potency of cocaine ($IC_{50}$=189 nM).

In HEK-hNET cells, the affinity of the compound for the binding site was higher than the affinity of cocaine, the standard compound, for the same site(s). The $K_1$ value for the displacement of [$I^{125}$] RTI-55 by 31,526 was 417 nM, and the $K_1$ value for cocaine displacement of [$I^{125}$] RTI-55 binding was 1730 nM. In the uptake assays, 31,526 was less potent at blocking the uptake of [$^3$H] norepinephrine, with an $IC_{50}$ value of 700 nM, as compared to the potency of cocaine ($IC_{50}$=209 nM).

Effects of 31,526 on HEK-hDAT, HEK-hSERT and HEK-hNET cells

|  | 31,526 | Cocaine |
|---|---|---|
| HEK-hDAT cells | | |
| [$I^{125}$] RTI-55 binding $K_1$(nM) | 38.7 ± 5.6 | 271 ± 65 |
| Hill coefficient | −0.86 ± 0.06 | −0.59 ± 0.06 |
| [$^3$H] Dopamine Uptake $IC_{50}$ (nM) | 460 ± 140 | 278 ± 23 |
| HEK-hSERT cells | | |
| [$I^{125}$] RTI-55 binding $K_1$(nM) | 30.0 ± 8.4 | 217 ± 23 |
| Hill coefficient | −1.12 ± 0.04 | −0.85 ± 0.06 |
| [$^3$H] Serotonin Uptake $IC_{50}$ (nM) | 192 ± 21 | 189 ± 31 |
| HEK-hNET cells | | |
| [$I^{125}$] RTI-55 binding $K_1$(nM) | 417 ± 34 | 1730 ± 280 |
| Hill coefficient | −0.91 ± 0.09 | −0.76 ± 0.05 |
| [$^3$H] NE Uptake $IC_{50}$ (nM) | 700 ± 240 | 209 ± 36 |

Numbers represent the means ± SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

Effects of 31,527 on HEK-hDAT, HEK-hSERT and HEK-hNET cells

|  | 31,527 | Cocaine |
|---|---|---|
| HEK-hDAT cells | | |
| [$I^{125}$] RTI-55 binding $K_1$(nM) | 26.5 ± 3.0 | 271 ± 65 |
| Hill coefficient | −0.84 ± 0.05 | −0.59 ± 0.06 |
| [$^3$H] Dopamine Uptake $IC_{50}$ (nM) | 610 ± 150 | 278 ± 53 |
| HEK-hSERT cells | | |
| [$I^{125}$] RTI-55 binding $K_1$(nM) | 34 ± 12 | 217 ± 23 |
| Hill coefficient | −0.98 ± 0.08 | −0.85 ± 0.06 |
| [$^3$H] Serotonin Uptake $IC_{50}$ (nM) | 440 ± 50 | 189 ± 31 |
| HEK-hNET cells | | |
| [$I^{125}$] RTI-55 binding $K_1$(nM) | 207 ± 20 | 1730 ± 280 |
| Hill coefficient | −0.72 ± 0.05 | −0.76 ± 0.05 |
| [$^3$H] NE Uptake $IC_{50}$ (nM) | 225 ± 28 | 209 ± 36 |

Numbers represent the means ± SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

EXAMPLE 5

Compound #31,527 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,527 was 26.5 nM, and the $K_i$ value for cocaine displacement of [$I^{125}$] RTI-55 binding was 217 nM. In the uptake assays 31,527 was less potent at blocking the uptake of [$^3$H] dopamine, with an $IC_{50}$ value of 610 nM, as compared to the potency of cocaine ($IC_{50}$=278 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55 by 31,527 was 34 nM, and the $K_1$ value for cocaine displacement of [$I^{125}$] RTI-55 binding was 217 nM. In the uptake assays, 31,527 was less potent at blocking the uptake of [$^3$H] serotonin, with an $IC_{50}$ value of 440 nM, as compared to the potency of cocaine ($IC_{50}$=189 nM).

In HEK-hNET cells, the affinity of the compound for the binding site was higher than the affinity of cocaine, the standard compound, for the same site(s). The $K_1$ value for the displacement of [$I^{125}$] RTI-55 by 31,527 was 207 nM, and the $K_1$ value for cocaine displacement of [$I^{125}$]RTI-55 binding was 1730 nM. In the uptake assays, 31,527 had about the same potency at blocking the uptake of [$^3$H] norepinephrine, with an $IC_{50}$ value of 255 nM, as compared to the potency of cocaine ($IC_{50}$=209 nM).

EXAMPLE 6

Compound #31,530 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,530 was 3.9 nM, and the $K_i$ value for cocaine displacement of [$I^{125}$] RTI-55 binding was 271 nM. In the uptake assays 31,530 was less potent at blocking the uptake of [$^3$H] dopamine, with an $IC_{50}$ value of 431 nM, as compared to the potency of cocaine ($IC_{50}$=278 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55 by 31,530 was 38 nM, and the $K_1$ value for cocaine displacement of [$I^{125}$] RTI-55 binding was 217 nM. In the uptake assays, 31,530 was less potent at blocking the uptake of [$^3$H] serotonin, with an $IC_{50}$ value of 3070 nM, as compared to the potency of cocaine ($IC_{50}$=189 nM).

In HEK-hNET cells, the affinity of the compound for the binding site was higher than the affinity of cocaine, the standard compound, for the same site(s). The $K_1$ value for the displacement of [$I^{125}$] RTI-55 by 31,530 was 250 nM, and the $K_1$ value for cocaine displacement of [$I^{125}$] RTI-55 binding was 1730 nM. In the uptake assays, 31,530 was less potent at blocking the uptake of [$^3$H] norepinephrine, with an $IC_{50}$ value of 1870 nM, as compared to the potency of cocaine ($IC_{50}$=209 nM).

Effects of 31,530 on HEK-hDAT, HEK-hSERT and HEK-hNET cells

|  | 31,530 | Cocaine |
|---|---|---|
| HEK-hDAT cells | | |
| [$I^{125}$] RTI-55 binding $K_1$(nM) | 3.9 ± 1.8 | 271 ± 65 |
| Hill coefficient | −0.59 ± 0.06 | −0.59 ± 0.06 |
| [$^3$H] Dopamine Uptake $IC_{50}$ (nM) | 431 ± 88 | 278 ± 53 |
| HEK-hSERT cells | | |
| [$I^{125}$] RTI-55 binding $K_1$(nM) | 38 ± 10 | 217 ± 23 |
| Hill coefficient | −0.74 ± 0.10 | −0.85 ± 0.06 |
| [$^3$H] Serotonin Uptake $IC_{50}$ (nM) | 3070 ± 830 | 189 ± 31 |
| HEK-hNET cells | | |
| [$I^{125}$] RTI-55 binding $K_1$(nM) | 250 ± 110 | 1730 ± 280 |
| Hill coefficient | −0.97 ± 0.30 | −0.76 ± 0.05 |
| [$^3$H] NE Uptake $IC_{50}$ (nM) | 1870 ± 670 | 209 ± 36 |

Numbers represent the means ± SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

Effects of 31,531 on HEK-hDAT, HEK-hSERT and HEK-hNET cells

|  | 31,531 | Cocaine |
|---|---|---|
| HEK-hDAT cells | | |
| [$I^{125}$] RTI-55 binding $K_1$(nM) | 6.4 ± 1.2 | 271 ± 65 |
| Hill coefficient | −0.63 ± 0.06 | −0.59 ± 0.06 |
| [$^3$H] Dopamine Uptake $IC_{50}$ (nM) | 96 ± 11 | 278 ± 23 |
| HEK-hSERT cells | | |
| [$I^{125}$] RTI-55 binding $K_1$(nM) | 17.9 ± 8.89 | 217 ± 23 |
| Hill coefficient | −0.64 ± 0.07 | −0.85 ± 0.06 |
| [$^3$H] Serotonin Uptake $IC_{50}$ (nM) | 1367 ± 41 | 189 ± 31 |
| HEK-hNET cells | | |
| [$I^{125}$] RTI-55 binding $K_1$(nM) | 54 ± 16 | 1730 ± 280 |
| Hill coefficient | −0.73 ± 0.03 | −0.76 ± 0.05 |
| [$^3$H] NE Uptake $IC_{50}$ (nM) | 179 ± 47 | 209 ± 36 |

Numbers represent the means ± SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

EXAMPLE 7

Compound #31,531 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and ($^3$H) serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,531 was 6.4 nM, and the $K_i$ value for cocaine displacement of [$I^{125}$] RTI-55 binding was 271 nM. In the uptake assays 31,531 was more potent at blocking the uptake of [$^3$H] dopamine, with an $IC_{50}$ value of 96 nM, as compared to the potency of cocaine (IC., =278 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55 by 31,531 was 17.9 nM, and the $K_1$ value for cocaine displacement of [$I^{125}$] RTI-55 binding was 217 nM. In the uptake assays, 31,531 had about the same potency at blocking the uptake of [$^3$H] serotonin, with an $IC_{50}$ value of 136 nM, as compared to the potency of cocaine ($IC_{50}$=189 nM).

In HEK-hNET cells, the affinity of the compound for the binding site was higher than the affinity of cocaine, the standard compound, for the same site(s). The $K_1$ value for the displacement of [$I^{125}$] RTI-55 by 31,531 was 54 nM, and the $K_1$ value for cocaine displacement of [$I^{125}$] RTI-55 binding was 1730 nM. In the uptake assays, 31,531 had about the same potency the uptake of [$^3$H] norepinephrine, with an $IC_{50}$ value of 179 nM, as compared to the potency of cocaine ($IC_{50}$=209 nM).

EXAMPLE 8

Compound #31,532 was tested for its effects on radioligand $I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,532 was 32.5 nM, and the $K_i$ value for cocaine displacement of [$I^{125}$] RTI-55 binding was 271 nM. In the uptake assays 31,532 had about the same potency at blocking the uptake of [$^3$H] dopamine, with an $IC_{50}$ value of 380 nM, as compared to the potency of cocaine ($IC_{50}$=278 nM). A Hill coefficient other than one suggests complex interactions with binding or uptake sites.

In HEK-hSERT cells, the affinity of the compound for the binding site was about the same as the affinity of cocaine, the standard compound, for the same site(s). The $K_1$ value for the displacement of [$I^{125}$] RTI-55 by 31,532 was 222 nM, and the $K_1$ value for cocaine displacement of [$I^{125}$] RTI-55 binding was 217 nM. In the uptake assays, 31,532 had about the same potency at blocking the uptake of [$^3$H] serotonin, with an $IC_{50}$ value of 3300 nM, as compared to the potency of cocaine ($IC_{50}$=189 nM).

In HEK-hNET cells, the affinity of the compound for the binding site was higher than the affinity of cocaine, the standard compound, for the same site(s). The $K_1$ value for the displacement of [$I^{125}$] RTI-55 by 31,532 was 221.6 nM, and the $K_1$ value for cocaine displacement of [$I^{125}$] RTI-55 binding was 1730 nM. In the uptake assays, 31,532 had about the same potency at blocking the uptake of [$^3$H] norepinephrine, with an $IC_{50}$ value of 310 nM, as compared to the potency of cocaine ($IC_{50}$=209 nM).

Effects of 31,532 on HEK-hDAT, HEK-hSERT and HEK-hNET cells

|  | 31,532 | Cocaine |
|---|---|---|
| HEK-hDAT cells | | |
| [$I^{125}$] RTI-55 binding $K_1$(nM) | 32.5 4.1 | 271 ± 65 |
| Hill coefficient | −0.87 ± 0.05 | −0.59 ± 0.06 |
| [$^3$H] Dopamine Uptake $IC_{50}$ (nM) | 380 ± 130 | 278 ± 53 |
| HEK-hSERT cells | | |
| [$I^{125}$] RTI-55 binding $K_1$(nM) | 222 ± 80 | 217 ± 23 |
| Hill coefficient | −0.80 ± 0.03 | −0.85 ± 0.06 |
| [$^3$H] Serotonin Uptake $IC_{50}$ (nM) | 3300 ± 1300 | 189 ± 31 |
| HEK-hNET cells | | |
| [$I^{125}$] RTI-55 binding $K_1$(nM) | 221.6 ± 9.7 | 1730 ± 280 |
| Hill coefficient | −0.80 ± 0.03 | −0.76 ± 0.05 |
| [$^3$H] NE Uptake $IC_{50}$ (nM) | 310 ± 100 | 209 ± 36 |

Numbers represent the means ± SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

EXAMPLE 9

CTDP 31,533 Alone Study

Method

The requisite starting materials also were prepared according to the procedures of J. Med. Chem., 1999, 42:3647–3656.

A dose response study of CTDP 31,533-induced locomotor activity was conducted according to the MDD locomotor activity studies standard operating procedure. The study was conducted using 16 Digiscan locomotor activity testing chambers (40.5×40.5×30.5 cm). Panels of infrared beams (16 beams) and corresponding photodetectors were located in the horizontal direction along the sides of each activity chamber. Separate groups of 8 non-habituated male Swiss-Webster mice were injected via the intraperitoneal (IP) route with either vehicle (sterile water) or CTDP 31,533 (1, 3, 10, or 30 mg/kg), immediately prior to locomotor activity testing. In all studies, horizontal activity (interruption of 1 photocell beam) was measured for 1-h within 10-min sample periods. Testing was conducted with one mouse per activity chamber.

Results

FIG. 1 shows average horizontal activity counts/10 min as a function of time, immediately following injection of CTDP 31,533 or vehicle. The period 30–60 min was selected for analysis of dose response data, because maximal stimulatant effects were obtained during this 30-min time period.

FIG. 2 shows average horizontal activity counts/10 min as a function of dose, immediately following injection of CTDP 31,533. Using TableCurve 3.05 software (Jandel Scientific), the mean average horizontal activity counts/10 min for this 30-min period were fit to a function of $\log_{10}$ dose, and the maximum effect was estimated from the resulting curve (maximum=1648.6 counts/10 min at 10.26 mg/kg). The estimated $ED_{50}$ (dose producing ½ maximal stimulant activity) was calculated to be 1.52 mg/kg from a linear regression against $\log_{10}$ dose of the ascending portion of the dose-effect curve (1–10 mg/kg CTDP 31,533). The $ED_{50}$ value was only an estimate due to a non-significant linear regression the dose-effect curve. The maximal effect/cocaine maximal effect ratio (ME/CNE) was equal to 0.30 based upon the maximum effect of 31,533 as estimated above and the maximum effect of cocaine previously estimated. (The maximum effect values were not corrected for control baseline.)

A one-way analysis of variance conducted on $\log_{10}$ horizontal activity counts for the 30–6-min time period indicated a significant overall effect F(4,35) 20.5, p<0.05; planned comparisons (a prior contrast) against the vehicle group showed significant differences for 1, 3, 10, and 30 mg/kg CTDP 31,533 (all ps<0.05 denoted in FIG. 2 with an asterisk).

EXAMPLE 10

CTDP 31,533/Cocaine Interaction Study

Method

The interaction study was conducted using 16 Digiscan locomotor activity testing chambers as described in the previous section. Immediately following IP vehicle or CTDP 31,533 injections (1,3, 10, or 30 mg/kg), groups of 8 non-habituated male Swiss-Webster mice were injected with either saline or 20 mg/kg cocaine IP and immediately placed in the Digiscan apparatus for a 1-h session.

Results

FIG. 3 shows average horizontal activity counts/10 min for the different treatment groups as a function of time. The period of 30–60 min was selected for analysis of dose-response data, because this is the time period in which cocaine produced its maximal effects.

FIG. 4 shows average horizontal activity counts/10 min for the different treatment groups as a function of dose. The bar above "vehicle" represents the effect of vehicle immediately following saline injection. The bar above "coc" represents the effect of 20 mg/kg cocaine immediately following the vehicle injection. The bars above "1, 3, 10, and 30" represent the effects of CTDP 31,533 at the designated doses following the cocaine injection. The mean average horizontal activity counts/10 min on the descending portion of the dose-effect curve (1 to 30 mg/kg dose range) for this 30-min period were fit to a linear function of $\log_{10}$ dose, and athe estimated $AD_{50}$ (dose attenuating cocaine-induced stimulation by 50%) was calculated to be 50.27 mg/kg. [The ordinate value for the $AD_{50}$ was calculated using the mean of the vehicle+0.9% saline (vehicle) group as the minimum value, and the mean of the vehicle plus 20 mg/kg cocaine (cocaine) group as the maximum value.]

A one-way analysis of variance conducted on $\log_{10}$ horizontal activity counts for the 0–30 min time period indicated a significant overall effect of treatment group, F(5,441)= 5.38, p<0.05; planned comparisons (a period contrast) against the cocaine group showed significant differences for vehicle and 30 mg/kg CTDP 31,533 (all ps<0.05 denoted in FIG. 4 with an asterisk).

EXAMPLE 11

CTDP 31.532 Alone Study

Method

A dose response study of CTDP 31,533-induced locomotor activity was conducted according to the MDD locomotor activity studies standard operating procedure. The study was conducted using 16 Digiscan locomotor activity testing chambers (40.5×40.5×30.5 cm). Panels of infrared beams (16 beams) and corresponding photodetectors were located in the horizontal direction along the sides of each activity chamber. Separate groups of 8 non-habituated male Swiss-Webster mice were injected via the intraperitoneal (IP) route with either vehicle (methylcellulose) or CTDP 31,533 (3, 10, 30, or 100 mg/kg), 20 minutes prior to locomotor activity testing. Just prior to placement in the apparatus, all mice received a saline injection IP. In all studies, horizontal activity (interruption of 1 photocell beam) was measured for I-h within 10-min periods. Testing was conducted with one mouse per activity chamber.

Results

FIG. 5 shows average horizontal activity counts/10 min as a function of time, starting 20 min after CTPD 31,532 pretreatment. The period 0–30 min was selected for analysis of dose response data, because this is the time period in which cocaine produced its maximal effects.

FIG. 6 shows average horizontal activity counts/10 min over 30 min as a function of dose, starting 20 min after CTDP 31,532 pretreatment. The mean average horizontal activity counts/10 min on the descending portion of the dose-effect curve (10 to 100 mg/kg dose range) for this 30-min period were fit to a linear function of $\log_{10}$ dose. The $ID_{50}$ (dose producing ½ maximal depressant activity, where maximal depression=0 counts/30 min) was calculated to be 112.95 mg/kg.

A one-way analysis of variance conducted on $\log_{16}$ horizontal activity counts/10 min for the 0–30-min time period indicated a significant overall effect $F(4,35)=6.04$, $p<0.05$; planned comparisons (a priori contrast) against vehicle group showed significant differences for 100 mg/kg dose only ($p<0.05$ denoted in FIG. 6 with an asterisk).

EXAMPLE 12

CTDP 31,532/Cocaine Interaction Study

Method

The interaction study was conducted using 16 Digiscan locomotor activity testing chambers as described in the previous section. Twenty minutes following IP vehicle or CTDP 31,532 injections (3, 10, 30, or 100 mg/kg), groups of 8 non-habituated male Swiss-Webster mice were injected with either 0.9% saline or 20 mg/kg cocaine Ip and immediately placed in the Digiscan apparatus for a 1-h session.

Results

FIG. 7 shows average horizontal activity counts/10 min for the different treatment groups as a function of time, starting 20 min after CTDP 31,532 pretreatment. The period of 0–30 min was selected for analysis of dose-response data, because this is the time period in which cocaine produced its maximal effects.

FIG. 8 shows average horizontal activity counts/10 min over 30 min as a function of dose condition, 20 min after CTDP 31,532 pretreatment. The bar above "vehicle" represents the effect of vehicle 20 min prior to saline injection. The bar above "coc" represents the effect of 20 mg/kg cocaine immediately following the vehicle injection. The bars above "3, 10, 30, and 100" represent the effects of CTDP 31,532 at the designated doses 20 min prior to 20 mg/kg cocaine injection. The mean average horizontal activity counts/10 min on the descending portion of the dose-effect curve (3 to 100 mg/kg dose range) for this 30-min period were fit to a linear function of $\log_{10}$ dose, and the estimated $AD_{50}$ (dose attenuating cocaine-induced stimulation by 50%) was calculated to be 18.35 mg/kg. [The ordinate value for the $AD_{50}$ was calculated using the mean of the vehicle+0.9% saline (vehicle) group as the minimum value, and the mean of the vehicle plus 20 mg/kg cocaine (cocaine) group as the maximum value.]

A one-way analysis of variance conducted on $\log_{10}$ horizontal activity counts for the 0–30 min time period indicated a significant overall effect of treatment group, $P(5,42)=6.38$, $p<0.05$; planned comparisons (a priori contrast) against the cocaine group showed significant differences for vehicle and the 100 mg/kg dose (all ps<0.05 denoted in FIG. 8 with an asterisk).

EXAMPLE 13

CTDP 31,530 Alone Study

Method

A dose response study of CTDP 31,530-induced locomotor activity was conducted according to the MDD locomotor activity studies standard operating procedure. The study was conducted using 16 Digiscan locomotor activity testing chambers (40.5×40.5×30.5 cm). Panels of infrared beams (16 beams) and corresponding photodetectors were located in the horizontal direction along the sides of each activity chamber. Separate groups of 8 non-habituated male Swiss-Webster mice were injected via the intraperitoneal (IP) route with either vehicle (sterile water) or CTDP 31,530(1, 3, 10, or 30 mg/kg), immediately prior to locomotor activity testing. In all studies, horizontal activity (interruption of 1 photocell beam) was measured for I-h within 10-min sample periods. Testing was conducted with one mouse per activity chamber.

Results

FIG. 9 shows average horizontal activity counts/10 min for the different treatment groups as a function of time, immediately following injection of CTDP 31,530 or vehicle. The period of 20–50 min was selected for analysis of dose-response data, because maximal stimulant effects were obtained during this 30 min time period.

FIG. 10 shows average horizontal activity counts/10 min as a function of time, immediately following injection of CTDP 31,530. Using TableCurve 3.05 software (Jandel Scientific), the mean average horizontal activity counts/10 min for this 30-min period were fit to a function of $\log_{10}$ dose, and the maximum effect was estimated from the resulting curve (maximum=2132.6 counts/10 min at 6.00 mg/kg). The estimated $ED_{50}$ (dose producing ½ maximal stimulant activity) was calculated to be 2.42 mg/kg from a linear regression against $\log_{10}$ dose of the ascending portion of the dose-effect curve (1–3 mg/kg CTDP 31,530). The maximal effect/cocaine maximal effect ratio (ME/CME) was equal to 0.38 based upon the maximum effect of 31,530 as estimated above and the maximum effect of cocaine previously estimated. (The maximum effect values were not corrected for control baseline.)

A one-way analysis of variance conducted on $\log_{10}$ horizontal activity counts for the 20–50-min time period indicated a significant overall effect $F(4,35)$ 14.0, $p<0.05$; planned comparisons (a priori contrast) against the vehicle group showed significant differences for 3, 10, and 30 mg/kg CTDP 31,530 (all ps<0.05 denoted in FIG. 10 with an asterisk).

EXAMPLE 14

CTDP 31,530/Cocaine Interaction Study

Method

The interaction study was conducted using 16 Digiscan locomotor activity testing chambers as described above. Immediately following IP vehicle or CTDP 31,530 injections (1,3, 10, or 30 mg/kg), groups of 8 non-habituated male Swiss-Webster mice were injected with either saline or 20 mg/kg cocaine IP and immediately placed in the Digiscan apparatus for a 1-h session.

Results

FIG. 11 shows average horizontal activity counts/10 min for the different treatment groups as a function of time. The period of 0–30 min was selected for analysis of dose-response data, because this is the time period in which cocaine produced its maximal effects.

FIG. 12 shows average horizontal activity counts/10 min for the different treatment groups as a function of dose. The bar above "vehicle" represents the effect of vehicle immediately following saline injection. The bar above "coc" represents the effect of 20 mg/kg cocaine immediately following the vehicle injection. The bars above "1, 3, 10, and 30" represent the effects of CTDP 31,530 at the designated doses following the cocaine injection. The mean average horizontal activity counts/10 min on the descending portion of the dose-effect curve (10 to 30 mg/kg dose range) for this 30-min period were fit to a linear function of $\log_{13}$ dose, and the estimated $AD_{50}$ (dose attenuating cocaine-induced stimulation by 50%) was calculated to be 15.75 mg/kg. [The ordinate value for the $AD_{50}$ was calculated using the mean of the vehicle+0.9% saline (vehicle) group as the minimum value, and the mean of the vehicle plus 20 mg/kg cocaine (cocaine) group as the maximum value.]

A one-way analysis of variance conducted on $\log_{10}$ horizontal activity a counts for the 0–30 min time period indicated a significant overall effect of treatment group, $F(5,42)=15.8$, $p<0.05$; planned comparisons (a priori contrast) against the cocaine group showed significant differences for vehicle and 30 mg/kg CTDP 31,530 (all $ps<0.05$ denoted in FIG. 12 with an asterisk).

EXAMPLE 15
CTDP 31.526 Alone Study
Method

A dose response study of CTDP 31,526-induced locomotor activity was conducted according to the MDD locomotor activity studies standard operating procedure. The study was conducted using 16 Digiscan locomotor activity testing chambers (40.5×40.5×30.5 cm). Panels of infrared beams (16 beams) and corresponding photodetectors were located in the horizontal direction along the sides of each activity chamber. Separate groups of 8 non-habituated male Swiss-Webster mice were injected via the intraperitoneal (IP) route with either vehicle (sterile water) or CTDP 31,526 (0.1, 1, 3, 10, or 30 mg/kg), 20 min prior to locomotor activity testing. Just prior to placement in the apparatus, all mice received a saline injection IP. In all studies, horizontal activity (interruption of 1 photocell beam) was measured for 1-h within 10-min sample periods. Testing was conducted with one mouse per activity chamber.
Results FIG. 13 shows average horizontal activity counts/10 min as a function of time, startin 20 min after CTDP 31,526 pretreatment. The period 0–30 min was selected for analysis of dose-response data, because maximal stimulant effects were obtained during this 30-min time period.

FIG. 14 shows average horizontal activity counts/10 min over 30 min as a function of dose, starting 20 min after CTDP 31,526 pretreatment. Using TableCurve 3.05 software (Jandel Scientific), the mean average horizontal activity counts/10 min for this 30-min period were fit to a function of $\log_{10}$ dose, and the maximum effect was estimated from the resulting curve (maximum=2716.1 counts/10 min at 0.64 mg/kg). The estimated $ED_{50}$ (dose producing ½ maximal stimulant activity) was calculated to be 0.015 mg/kg from a linear regression against $\log_{10}$ dose of the ascending portion of the dose-effect curve (0.1–1 mg/kg CTDP 31,526). The $ED_{50}$ value was only an estimate due to a non-significant linear regression the dose-effect curve. The maximal effect/cocaine maximal effect ration (ME/CNE) was equal to 0.49 based upon the maximum effect of 31,526 as estimated above and the maximum effect of cocaine previously estimated. (The maximum effect values were not corrected for control baseline.) A one-way analysis of variance conducted on $\log_{10}$ horizontal activity counts for the 0–30 min time period indicated a significant overall effect $F(5,42)$ 2.07; planned comparisons (a prior contrast) against the vehicle group showed significant differences for 1 mg/kg CTDP 31,526 only ($p<0.05$ denoted in FIG. 14 with an asterisk).

EXAMPLE 16
CTDP 31,526/Cocaine Interaction Study
Method

The interaction study was conducted using 16 Digiscan locomotor activity testing chambers as described in the previous section. Twenty minutes following IP vehicle or CTDP 31,526 injections (0.1, 1,3, or 10 mg/kg), groups of 8 non-habituated male Swiss-Webster mice were injected with either saline or 20 mg/kg cocaine IP and immediately placed in the Digiscan apparatus for a 1-h session.
Results FIG. 15 shows average horizontal activity counts/10 min for the different treatment groups as a function of time. The period of 0–30 min was selected for analysis of dose-response data, because this is the time period in which cocaine produced its maximal effects.

FIG. 16 shows average horizontal activity counts/10 min for the different treatment groups as a function of dose. The bar above "vehicle" represents the effect of vehicle immediately following saline injection. The bar above "coc" represents the effect of 20 mg/kg cocaine immediately following the vehicle injection. The bars above "0.1, 1, 3, and 10" represent the effects of CTDP 31,526 at the designated doses following the cocaine injection. CTDP 31,526 did not attenuate locomotor activity induced by 20 mg/kg cocaine; therefore an $AD_{50}$ was not calculated.

A one-way analysis of variance conducted on $\log_{10}$ horizontal activity counts for the 0–30 min time period indicated a significant overall effect of treatment group, $F(4,35)=16.1$, $p<0.05$; planned comparisons (a prior contrast) against the cocaine group showed significant differences for vehicle only ($p<0.05$ denoted in FIG. 16 with an asterisk).

EXAMPLE 17

Compound #31,628 was tested for its effects on radioligand ($[I^{125}]$ RTI-55) binding to and $[^3H]$ dopamine uptake by HEK cells expressing cDNA for the human dopamine transporter (HEK-hDAT cells), its effect on radioligand ($[I^{125}]$ RTI-55) binding and $[^3H]$ serotonin uptake by HEK cells expressing cDNA for the human serotonin transporter (HEK-hSERT cells), and its effects on radioligand ($[I^{125}]$ RTI-55) binding and $[^3H]$ norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of $[I^{125}]$ RTI-55 by 31,628 was 94 nM, and the $K_i$ value for cocaine displacement of $[I^{125}]$ RTI-55 binding was 573 nM. In the uptake assays 31,628 had about the same potency at blocking the uptake of $[^3H]$ dopamine, with an $IC_{50}$ value of 56 nM, as compared to the potency of cocaine ($IC_{50}=237$ nM). A Hill coefficient other than one suggests complex interactions with binding or uptake sites.

In HEK-hSERT cells, the affinity of the compound for the binding site was about the same as the affinity of cocaine, the standard compound, for the same site(s). The K, value for the displacement of $[I^{125}]$ RTI-55 by 31,628 was 132 nM, and the $K_1$ value for cocaine displacement of $[I^{125}]$ RTI-55 binding was 402 nM. In the uptake assays, 31,628 had about the same potency at blocking the uptake of $[^3H]$ serotonin, with an $IC_{50}$ value of 203 nM, as compared to the potency of cocaine ($IC_{50}=348$ nM).

In HEK-hNET cells, the affinity of the compound for the binding site was higher than the affinity of cocaine, the standard compound, for the same site(s). The $K_1$ value for the displacement of $[I^{125}]$ RTI-55 by 31,628 was 578 nM, and the $K_1$ value for cocaine displacement of $[I^{125}]$ RTI-55 binding was 2040 nM. In the uptake assays, 31,628 had about the same potency at blocking the uptake of $[^3H]$ norepinephrine, with an $IC_{50}$ value of 158 nM, as compared to the potency of cocaine ($IC_{30}$=190 nM).

Effects of 31,628 on HEK-hDAT, HEK-hSERT and HEK-hNET cells

|  | 31,628 | Cocaine |
|---|---|---|
| HEK-hDAT cells |  |  |
| $[I^{125}]$ RTI-55 binding $K_1$(nM) | 94 ± 42 | 573 ± 54 |
| Hill coefficient | −1.02 ± 0.16 | −0.89 ± 0.07 |
| $[^3H]$ Dopamine Uptake $IC_{50}$ (nM) | 56 ± 16 | 237 ± 41 |
| HEK-hSERT cells |  |  |
| $[I^{125}]$ RTI-55 binding $K_1$(nM) | 132 ± 26 | 402 ± 62 |
| Hill coefficient | −0.84 ± 0.02 | −1.09 ± 0.09 |
| $[^3H]$ Serotonin Uptake $IC_{50}$ (nM) | 203 ± 78 | 348 ± 66 |
| HEK-hNET cells |  |  |
| $[I^{125}]$ RTI-55 binding $K_1$(nM) | 578 ± 52 | 2040 ± 240 |
| Hill coefficient | −1.48 ± 0.70 | −1.14 ± 0.11 |
| $[^3H]$ NE Uptake $IC_{50}$ (nM) | 158 ± 60 | 190 ± 38 |

Numbers represent the means ± SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

EXAMPLE 18

Compound #31,627 was tested for its effects on radioligand ($[I^{125}]$ RTI-55) binding to and $[^3H]$ dopamine uptake by HEK cells expressing cDNA for the human dopamine transporter (HEK-hDAT cells), its effect on radioligand ($[I^{125}]$ RTI-55) binding and $[^3H]$ serotonin uptake by HEK cells expressing cDNA for the human serotonin transporter (HEK-hSERT cells), and its effects on radioligand ($[I^{125}]$ RTI-55) binding and $[^3H]$ norepinephrine uptake by HEK cells expressing cDNA for the human norepinephrine transporter (HEK-hNET cells).

In HEK-hDAT cells, the affinity of the compound for the binding site was lower than the affinity of cocaine, the standard compound, for the same site(s). The $K_i$ value for the displacement of $[I^{125}]$ RTI-55 by 31,627 was greater than 10 μM, and the $K_i$ value for cocaine displacement of $[I^{125}]$ RTI-55 binding was 573 nM. Uptake assays are not conducted when the $K_1$ value is greater than 10 μM. A Hill coefficient other than one suggests complex interactions with binding or uptake sites.

In HEK-hSERT cells, the affinity of the compound for the binding site was lower than the affinity of cocaine, the standard compound, for the same site(s). The $K_1$ value for the displacement of $[I^{125}]$ RTI-55 by 31,627 was 1591 nM, and the $K_1$ value for cocaine displacement of $[I^{125}]$ RTI-55 binding was 402 nM. In the uptake assays, 31,627 had about the same potency at blocking the uptake of $[^3H]$ serotonin, with an $IC_{50}$ value of 361 nM, as compared to the potency of cocaine ($IC_{50}$=348 nM).

In HEK-hNET cells, the affinity of the compound for the binding site was higher than the affinity of cocaine, the standard compound, for the same site(s). The $K_1$ value for the displacement of $[I^{125}]$ RTI-55 by 31,627 was greater than 10 μM, and the $K_1$ value for cocaine displacement of $[I^{125}]$ RTI-55 binding was 2040 nM. Uptake assays are not conducted when the $K_1$ value is greater than 10 μM.

Effects of 31,627 on HEK-hDAT, HEK-hSERT and HEK-hNET cells

|  | 31,627 | Cocaine |
|---|---|---|
| HEK-hDAT cells |  |  |
| $[I^{125}]$ RTI-55 binding $K_1$ (nM) | >10 μM | 573 ± 54 |
| Hill coefficient |  | −0.89 ± 0.07 |
| $[^3H]$ Dopamine Uptake $IC_{50}$ (nM) |  | 237 ± 41 |
| HEK-hSERT cells |  |  |
| $[I^{125}]$ RTI-55 binding $K_1$ (nM) | 1591 ± 43 | 402 ± 62 |
| Hill coefficient | −1.01 ± 0.08 | −1.04 ± 0.05 |
| $[^3H]$ Serotonin Uptake $IC_{50}$ (nM) | 361 ± 68 | 348 ± 66 |
| HEK-hNET cells |  |  |
| $[I^{125}]$ RTI-55 binding $K_1$ (nM) | >10 μM | 2040 ± 240 |
| Hill coefficient |  | −1.14 ± 0.11 |
| $[^3H]$ NE Uptake $IC_{50}$ (nM) |  | 190 ± 38 |

Numbers represent the means ± SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

EXAMPLE 19

Compound #31,626 was tested for its effects on radioligand ($[I^{125}]$ RTI-55) binding to and $[^3H]$ dopamine uptake by HEK cells expressing cDNA for the human dopamine transporter (HEK-hDAT cells), its effect on radioligand ($[I^{125}]$ ill, RTI-55) binding and $[^3H]$ serotonin uptake by HEK cells expressing cDNA for the human serotonin transporter (HEK-hSERT cells), and its effects on radioligand ($[I^{125}]$ RTI-55) binding and $[^3H]$ norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of $[I^{125}]$ RTI-55 by 31,626 was 67 nM, and the $K_i$ value for cocaine displacement of $[I^{125}]$ RTI-55 binding was 573 nM. In the uptake assays 31,626 was less potent at blocking the uptake of $[^3H]$ dopamine, with an $IC_{50}$ value of 328 nM, as compared to the potency of cocaine ($IC_{50}$=237 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of $[I^{125}]$ RTI-55 by 31,626 was 88 nM, and the $K_1$ value for cocaine displacement of $[I^{125}]$ RTI-55 binding was 402 nM. In the uptake assays, 31,626 was more potent at blocking the uptake of $[^3H]$ serotonin, with an $IC_{50}$ value of 119 nM, as compared to the potency of cocaine ($IC_{50}$=348 nM).

In HEK-hNET cells, the affinity of the compound for the binding site was higher than the affinity of cocaine, the standard compound, for the same site(s). The $K_1$ value for the displacement of $[I^{125}]$ RTI-55 by 31,626 was 540 nM, and the $K_1$ value for cocaine displacement of $[I^{125}]$ RTI-55 binding was 2040 nM. In the uptake assays, 31,626 had about the same potency at blocking the uptake of $[^3H]$ norepinephrine, with an $IC_{50}$ value of 190 nM, as compared to the potency of cocaine ($IC_{50}$=190 nM).

| Effects of 31,626 on HEK-hDAT, HEK-hSERT and HEK-hNET cells | | |
| --- | --- | --- |
| | 31,626 | Cocaine |
| HEK-hDAT cells | | |
| [$I^{125}$] RTI-55 binding $K_1$ (nM) | 67 ± 10 | 573 ± 54 |
| Hill coefficient | −1.11 ± 0.08 | −0.89 ± 0.07 |
| [$^3$H] Dopamine Uptake $IC_{50}$ (nM) | 328 ± 34 | 237 ± 41 |
| HEK-hSERT cells | | |
| [$I^{125}$] RTI-55 binding $K_1$ (nM) | 88 ± 29 | 402 ± 62 |
| Hill coefficient | −0.89 ± 0.06 | −1.04 ± 0.09 |
| [$^3$H] Serotonin Uptake $IC_{50}$ (nM) | 119 ± 33 | 348 ± 66 |
| HEK-hNET cells | | |
| [$I^{125}$] RTI-55 binding $K_1$ (nM) | 540 ± 180 | 2040 ± 240 |
| Hill coefficient | −1.39 ± 0.23 | −1.14 ± 0.11 |
| [$^3$H] NE Uptake $IC_{50}$ (nM) | 290 ± 110 | 190 ± 38 |

Numbers represent the means ± SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

| Effects of 31,625 on HEK-hDAT, HEK-hSERT and HEK-hNET cells | | |
| --- | --- | --- |
| | 31,625 | Cocaine |
| HEK-hDAT cells | | |
| [$I^{125}$] RTI-55 binding $K_1$ (nM) | 4.2 ± 2.1 | 573 ± 54 |
| Hill coefficient | −0.74 ± 0.25 | −0.89 ± 0.07 |
| [$^3$H] Dopamine Uptake $IC_{50}$ (nM) | 400 ± 170 | 237 ± 41 |
| HEK-hSERT cells | | |
| [$I^{125}$] RTI-55 binding $K_1$ (nM) | >10 μM | 402 ± 62 |
| Hill coefficient | | −1.09 ± 0.09 |
| [$^3$H] Serotonin Uptake $IC_{50}$ (nM) | | |
| HEK-hNET cells | | |
| [$I^{125}$] RTI-55 binding $K_1$ (nM) | 217 ± 16 | 2040 ± 240 |
| Hill coefficient | −0.99 ± 0.22 | −1.14 ± 0.11 |
| [$^3$H] NE Uptake $IC_{50}$ (nM) | 800 ± 340 | 190 ± 38 |

Numbers represent the means ± SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

EXAMPLE 20

Compound #31,625 was tested for its effects on radioligand ([$I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,625 was 4.2 nM, and the $K_i$ value for cocaine displacement of [$I^{125}$] RTI-55 binding was 573 nM. In the uptake assays 31,625 had about the same potency at blocking the uptake of [$^3$H] dopamine, with an $IC_{50}$ value of 400 mM, as compared to the potency of cocaine ($IC_{50}$=237 nM). A Hill coefficient other than one suggests complex interactions with binding or uptake sites.

In HEK-hSERT cells, the affinity of the compound for the binding site lower than the affinity of cocaine, the standard compound, for the same site(s). The $K_1$ value for the displacement of [$I^{125}$] RTI-55 by 31,625 was greater than 10 μM, and the $K_1$ value for cocaine displacement of [$I^{125}$] RTI-SS binding was 402 nM. Uptake assays are not conducted when the $K_1$ value is greater than 10 μM.

In HEK-hNET cells, the affinity of the compound for the binding site was higher than the affinity of cocaine, the standard compound, for the same site(s). The $K_1$ value for the displacement of [$I^{125}$] RTI-55 by 31,625 was 217 nM, and the $K_1$ value for cocaine displacement of [$I^{125}$] RTI-55 binding was 2040 nM. In the uptake assays, 31,625 was less potent at blocking the uptake of [$^3$H] norepinephrine, with an $IC_{50}$ value of 800 nM, as compared to the potency of cocaine ($IC_{50}$=190 nM).

EXAMPLE 21

Compound #31,648 was tested for its effects on radioligand ([$I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,648 was 114 nM, and the $K_i$ value for cocaine displacement of ($I^{125}$) RTI-55 binding was 258 nM. In the uptake assays 31,648 was more potent at blocking the uptake of [$^3$H] dopamine, with an $IC_{50}$ value of 101 nM, as compared to the potency of cocaine ($IC_{50}$=276 nM). A Hill coefficient other than one suggests complex interactions with binding or uptake sites.

In HEK-hSERT cells, the affinity of the compound for the binding site was about the same as the affinity of cocaine, the standard compound, for the same site(s). The $K_1$ value for the displacement of [$I^{125}$] RTI-55 by 31,648 was 423 nM, and the $K_1$ value for cocaine displacement of [$I^{125}$] RTI-55 binding was 343 nM. In the uptake assays 31,648 had about the same potency at blocking the uptake of [$^3$H] serotonin, with an $IC_{50}$ value of 314 nM, as compared to the potency of cocaine ($IC_{50}$=301 nM).

In HEK-hNET cells, the affinity of the compound for the binding site was higher than the affinity of cocaine, the standard compound, for the same site(s). The $K_1$ value for the displacement of [$I^{125}$] RTI-55 by 31,648 was 610 nM, and the $K_1$ value for cocaine displacement of [$I^{125}$] RTI-55 binding was 1740 nM. In the uptake assays, 31,648 was more potent at blocking the uptake of [$^3$H] norepinephrine, with an $IC_{50}$ value of 143 nM, as compared to the potency of cocaine ($IC_{50}$=264 nM).

| Effects of 31,648 on HEK-hDAT, HEK-hSERT and HEK-hNET cells | | |
|---|---|---|
| | 31,648 | Cocaine |
| HEK-hDAT cells | | |
| [I$^{125}$] RTI-55 binding K$_1$ (nM) | 114 ± 27 | 258 ± 23 |
| Hill coefficient | −0.69 ± 0.07 | −0.76 ± 0.05 |
| [$^3$H] Dopamine Uptake IC$_{50}$ (nM) | 101 ± 11 | 276 ± 22 |
| HEK-hSERT cells | | |
| [I$^{125}$] RTI-55 binding K$_1$ (nM) | 423 ± 98 | 343 ± 31 |
| Hill coefficient | −0.95 ± 0.07 | −0.97 ± 0.08 |
| [$^3$H] Serotonin Uptake IC$_{50}$ (nM) | 314 ± 71 | 301 ± 53 |
| HEK-hNET cells | | |
| [I$^{125}$] RTI-55 binding K$_1$ (nM) | 610 ± 130 | 1740 ± 180 |
| Hill coefficient | −0.75 ± 0.06 | −0.71 ± 0.03 |
| [$^3$H] NE Uptake IC$_{50}$ (nM) | 143 ± 50 | 264 ± 57 |

Numbers represent the means ± SEM from at least three independent experiments, each conducted with duplicate (for binding assays) or triplicate (for uptake assays) determinations. When the K$_1$ or the IC$_{50}$ for the test compound is greater than 10 μM, only two experiments are conducted and no standard error is reported.

EXAMPLE 22

Compound #31,649 was tested for its effects on radioligand ([I$^{125}$] RTI-55) binding to and [$^3$H] dopamine uptake by HEK cells expressing cDNA for the human dopamine transporter (HEK-hDAT cells), its effect on radioligand ([I$^{125}$] RTI-55) binding and [$^3$H] serotonin uptake by HEK cells expressing cDNA for the human serotonin transporter (HEK-hSERT cells), and its effects on radioligand ([I$^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The K$_i$ value for the displacement of [I$^{125}$] RTI-55 by 31,649 was 1.32 nM, and the K$_i$ value for cocaine displacement of [I$^{125}$] RTI-55 binding was 258 nM. In the uptake assays 31,649 was less potent at blocking the uptake of [$^3$H] dopamine, with an IC$_{50}$ value of 426 nM, as compared to the potency of cocaine (IC$_{50}$=276 nM). A Hill coefficient other than one suggests complex interactions with binding or uptake sites.

In HEK-hSERT cells, the affinity of the compound for the binding site was higher than the affinity of cocaine, the standard compound, for the same site(s). The K$_1$ value for the displacement of [I$^{125}$] RTI-55 by 31,649 was 3.8 nM, and the K$_1$ value for cocaine displacement of [I$^{125}$] RTI-55 binding was 343 nM.

In the uptake assays, 31,649 was less potent at blocking the uptake of [$^3$H] serotonin, with an IC$_{50}$ value of 570 nM, as compared to the potency of cocaine (IC$_{50}$=301 nM).

In HEK-hNET cells, the affinity of the compound for the binding site was higher than the affinity of cocaine, the standard compound, for the same site(s). The K$_1$ value for the displacement of [I$^{125}$] RTI-55 by 31,649 was 22.2 nM, and the K$_1$ value for cocaine displacement of [I$^{125}$] RTI-55 binding was 1740 nM. In the uptake assays, 31,649 was more potent at blocking the uptake of [$^3$H] norepinephrine, with an IC$_{50}$ value of 132 nM, as compared to the potency of cocaine (IC$_{50}$=264 nM).

| Effects of 31,649 on HEK-hDAT, HEK-hSERT and HEK-hNET cells | | |
|---|---|---|
| | 31,649 | Cocaine |
| HEK-hDAT cells | | |
| [I$^{125}$] RTI-55 binding K$_1$ (nM) | 1.32 ± 0.49 | 258 ± 23 |
| Hill coefficient | −0.63 ± 0.23 | −0.76 ± 0.05 |
| [$^3$H] Dopamine Uptake IC$_{50}$ (nM) | 426 ± 54 | 276 ± 22 |
| HEK-hSERT cells | | |
| [I$^{125}$] RTI-55 binding K$_1$ (nM) | 3.8 ± 1.9 | 343 ± 31 |
| Hill coefficient | −0.55 ± 0.06 | −0.97 ± 0.08 |
| [$^3$H] Serotonin Uptake IC$_{50}$ (nM) | 570 ± 210 | 301 ± 53 |
| HEK-hNET cells | | |
| [I$^{125}$] RTI-55 binding K$_1$ (nM) | 22.2 ± 3.6 | 1740 ± 180 |
| Hill coefficient | −0.47 ± 0.03 | −0.71 ± 0.03 |
| [$^3$H] NE Uptake IC$_{50}$ (nM) | 132 ± 11 | 264 ± 57 |

Numbers represent the means ± SEM from at least three independent experiments, each conducted with duplicate (for binding assays) or triplicate (for uptake assays) determinations. When the K$_1$ or the IC$_{50}$ for the test compound is greater than 10 μM, only two experiments are conducted and no standard error is reported.

EXAMPLE 23

Compound #31,650 was tested for its effects on radioligand ([I$^{125}$] RTI-55) binding to and [$^3$H] dopamine uptake by HEK cells expressing cDNA for the human dopamine transporter (HEK-hDAT cells), its effect on radioligand ([I$^{125}$] RTI-55) binding and [$^3$H] serotonin uptake by HEK cells expressing cDNA for the human serotonin transporter (HEK-hSERT cells), and its effects on radioligand ([I$^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The K$_i$ value for the displacement of [I$^{125}$] RTI-55 by 31,650 was 91 nM, and the K$_i$ value for cocaine displacement of [I$^{125}$] RTI-55 binding was 258 nM. In the uptake assays 31,650 was more poent at blocking the uptake of [$^3$H] dopamine, with an IC$_{50}$ value of 114 nM, as compared to the potency of cocaine (IC$_{50}$=276 nM). A Hill coefficient other than one suggests complex interactions with binding or uptake sites.

In HEK-hSERT cells, the affinity of the compound for the binding site was about the same as the affinity of cocaine, the standard compound, for the same site(s). The K$_1$ value for the displacement of [I$^{125}$] RTI-55 by 31,650 was greater than 437 nM, and the K$_1$ value for cocaine displacement of [I$^{125}$] RTI-55 binding was 343 nM. In the uptake assays, 31,650 had was less potent at blocking the uptake of [$^3$H] serotonin, with an IC$_{50}$ value of 860 nM, as compared to the potency of cocaine (IC$_{50}$=301 nM).

In HEK-hNET cells, the affinity of the compound for the binding site was higher than the affinity of cocaine, the standard compound, for the same site(s). The K$_1$ value for the displacement of [I$^{125}$] RTI-55 by 31,650 was 611 nM, and the K$_1$ value for cocaine displacement of [I$^{125}$] RTI-55 binding was 1740 nM. In the uptake assays, 31,650 had about the same potency at blocking the uptake of [$^3$H] norepinephrine, with an IC$_{50}$ value of 310 nM, as compared to the potency of cocaine (IC$_{50}$ 264 nM).

| Effects of 31,650 on HEK-hDAT, HEK-hSERT and HEK-hNET cells | | |
| --- | --- | --- |
|  | 31,650 | Cocaine |
| HEK-hDAT cells | | |
| [$I^{125}$] RTI-55 binding $K_1$ (nM) | 91 ± 26 | 258 ± 23 |
| Hill coefficient | −0.82 ± 0.15 | −0.76 ± 0.05 |
| [$^3$H] Dopamine Uptake $IC_{50}$ (nM) | 114 ± 28 | 276 ± 22 |
| HEK-hSERT cells | | |
| [$I^{125}$] RTI-55 binding $K_1$ (nM) | 437 ± 66 | 343 ± 31 |
| Hill coefficient | −0.75 ± 0.12 | −0.97 ± 0.08 |
| [$^3$H] Serotonin Uptake $IC_{50}$ (nM) | 860 ± 180 | 301 ± 31 |
| HEK-hNET cells | | |
| [$I^{125}$] RTI-55 binding $K_1$ (nM) | 611 ± 76 | 1740 ± 180 |
| Hill coefficient | −0.66 ± 0.05 | −0.71 ± 0.03 |
| [$^3$H] NE Uptake $IC_{50}$ (nM) | 310 ± 110 | 264 ± 57 |

Numbers represent the means ± SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

| Effects of 31,652 on HEK-hDAT, HEK-hSERT and HEK-hNET cells | | |
| --- | --- | --- |
|  | 31,652 | Cocaine |
| HEK-hDAT cells | | |
| [$I^{125}$] RTI-55 binding $K_1$ (nM) | 50 ± 12 | 258 ± 23 |
| Hill coefficient | −1.08 ± 0.18 | −0.76 ± 0.05 |
| [$^3$H] Dopamine Uptake $IC_{50}$ (nM) | 1170 ± 250 | 276 ± 22 |
| HEK-hSERT cells | | |
| [$I^{125}$] RTI-55 binding $K_1$ (nM) | 33 ± 11 | 343 ± 31 |
| Hill coefficient | −0.81 ± 0.06 | −0.97 ± 0.08 |
| [$^3$H] Serotonin Uptake $IC_{50}$ (nM) | 320 ± 120 | 301 ± 53 |
| HEK-hNET cells | | |
| [$I^{125}$] RTI-55 binding $K_1$ (nM) | 3800 ± 130 | 1740 ± 180 |
| Hill coefficient | −0.80 ± 0.08 | −0.71 ± 0.03 |
| [$^3$H] NE Uptake $IC_{50}$ (nM) | 390 ± 130 | 264 ± 57 |

Numbers represent the means ± SEM from at least three independent experiments, each conducted with duplicate (for binding assays) or triplicate (for uptake assays) determinations. When the $K_1$ or the $IC_{50}$ for the test compound is greater than 10 μM, only two experiments are conducted and no standard error is reported.

EXAMPLE 24

Compound #31,652 was tested for its effects on radioligand ([$I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,652 was 50 nM, and the $K_i$ value for cocaine displacement of [$I^{125}$] RTI-55 binding was 258 nM. In the uptake assays 31,652 was less potent at blocking the uptake of [$^3$H] dopamine, with an $IC_{50}$ value of 1170 nM, as compared to the potency of cocaine ($IC_{50}$=276 mM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55 by 31,652 was 33 nM and the $K_1$ value for cocaine displacement of [$I^{125}$] RTI-55 binding was 343 nM. In the uptake assays 31,652 had about the same potency at blocking the uptake of [$^3$H] serotonin, with an $IC_{50}$ value of 320 nM, as compared to the potency of cocaine ($IC_{50}$=301 nM).

In HEK-hNET cells, the affinity of the compound for the binding site was higher than the affinity of cocaine, the standard compound, for the same site(s). The $K_1$ value for the displacement of [$I^{125}$] RTI-55 by 31,652 was 380 nM, and the $K_1$ value for cocaine displacement of [$I^{125}$] RTI-55 binding was 1740 nM. In the uptake assays 31,652 had about the same potency at blocking the uptake of [$^3$H] norepinephrine, with an $IC_{50}$ value of 390 nM, as compared to the potency of cocaine ($IC_{50}$=264 nM).

EXAMPLE 25

Compound #31,653 was tested for its effects on radioligand ([$I^{125}$] RTI-55) binding to and [$^3$H] dopamine uptake by HEK cells expressing cDNA for the human dopamine transporter (HEK-hDAT cells), its effect on radioligand ([$I^{125}$] RTI-55) binding and [$^3$H] serotonin uptake by HEK cells expressing cDNA for the human serotonin transporter (HEK-hSERT cells), and its effects on radioligand ([$I^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The $K_i$ value for the displacement of [$I^{125}$] RTI-55 by 31,653 was 60.9 nM, and the $K_i$ value for cocaine displacement of [$I^{125}$] RTI-55 binding was 258 nM. In the uptake assays 31,653 was less potent at blocking the uptake of [$^3$H] dopamine, with an $IC_{50}$ value of 1410 nM, as compared to the potency of cocaine ($IC_{50}$=276 nM). A Hill coefficient other than one suggests complex interactions with binding or uptake sites.

In HEK-hSERT cells, the affinity of the compound for the binding site was higher than the affinity of cocaine, the standard compound, for the same site(s). The $K_1$ value for the displacement of [$I^{125}$] RTI-55 by 31,653 was 51 nM, and the $K_1$ value for cocaine displacement of [$I^{125}$] RTI-55 binding was 343 nM. In the uptake assays, 31,653 was less potent at blocking the uptake of [$^3$H] serotonin, with an $IC_{50}$ value of 1020 nM, as compared to the potency of cocaine ($IC_{50}$=301 nM).

In HEK-hNET cells, the affinity of the compound for the binding site was higher than the affinity of cocaine, the standard compound, for the same site(s). The $K_1$ value for the displacement of [$I^{125}$] RTI-55 by 31,653 was 203 nM, and the $K_1$ value for cocaine displacement of [$I^{125}$] RTI-55 binding was 1740 nM. In the uptake assays, 31,653 was more potent at blocking the uptake of [$^3$H] norepinephrine, with an $IC_{50}$ value of 56.3 nM, as compared to the potency of cocaine ($IC_{50}$=264 nM).

| | 31,653 | Cocaine |
|---|---|---|
| *Effects of 31,653 on HEK-hDAT, HEK-hSERT and HEK-hNET cells* | | |
| HEK-hDAT cells | | |
| [I$^{125}$] RTI-55 binding K$_1$ (nM) | 60.9 ± 6.4 | 258 ± 23 |
| Hill coefficient | −1.14 ± 0.10 | −0.76 ± 0.05 |
| [$^3$H] Dopamine Uptake IC$_{50}$ (nM) | 1410 ± 580 | 276 ± 22 |
| HEK-hSERT cells | | |
| [I$^{125}$] RTI-55 binding K$_1$ (nM) | 51 ± 18 | 343 ± 31 |
| Hill coefficient | −0.81 ± 0.05 | −0.97 ± 0.08 |
| [$^3$H] Serotonin Uptake IC$_{50}$ (nM) | 1020 ± 320 | 301 ± 53 |
| HEK-hNET cells | | |
| [I$^{125}$] RTI-55 binding K$_1$ (nM) | 203 ± 76 | 1740 ± 180 |
| Hill coefficient | −0.93 ± 0.17 | −0.71 ± 0.03 |
| [$^3$H] NE Uptake IC$_{50}$ (nM) | 56.3 ± 9.4 | 264 ± 57 |

Numbers represent the means ± SEM from at least three independent experiments, each conducted with duplicate (for binding assays) or triplicate (for uptake assays) determinations. When the K$_1$ or the IC$_{50}$ for the test compound is greater than 10 μM, only two experiments are conducted and no standard error is reported.

EXAMPLE 26

Compound #31,654 was tested for its effects on radioligand ([I$^{125}$] RTI-55) binding to and [$^3$H] dopamine uptake by HEK cells expressing cDNA for the human dopamine transporter (HEK-hDAT cells), its effect on radioligand ([I$^{125}$] RTI-55) binding and [$^3$H] serotonin uptake by HEK cells expressing cDNA for the human serotonin transporter (HEK-hSERT cells), and its effects on radioligand ([I$^{125}$] RTI-55) binding and [$^3$H] norepinephrine uptake by HEK cells expressing cDNA for the human norepinephrine transporter (HEK-hNET cells).

In HEK-hDAT cells, the affinity of the compound for the binding site was higher than the affinity of cocaine, the standard compound, for the same site(s). The K$_i$ value for the displacement of [I$^{125}$] RTI-55 by 31,654 was 26.2 nM, and the K$_i$ value for cocaine displacement of [I$^{125}$] RTI-55 binding was 258 nM. In the uptake assays 31,654 had about the same potency at blocking the uptake of [$^3$H] dopamine, with an IC$_{50}$ value of 301 nM, as compared to the potency of cocaine (IC$_{50}$=276 nM). A Hill coefficient other than one suggests complex interactions with binding or uptake sites.

In HEK-hSERT cells, the affinity of the compound for the binding site was about the same as the affinity of cocaine, the standard compound, for the same site(s). The K$_1$ value for the displacement of the K$_1$ value for the displacement of [I$^{125}$] RTI-55 by 31,654 was 255 nM and the K$_1$ value for cocaine displacement of [I$^{125}$] RTI-55 binding was 343 nM. In the uptake assays, 31,654 had about the same potency at blocking the uptake of [$^3$H] dopamine, with an IC$_{50}$ value of 301 nM, as compared to the potency of cocaine (IC$_{50}$=276 nM). A Hill coefficient other than one suggests complex interactions with binding or uptake sites.

In HEK-hNET cells, the affinity of the compound for the binding site was higher than the affinity of cocaine, the standard compound, for the same site(s). The K$_1$ value for the displacement of [I$^{125}$] RTI-55 by 31,654 was 92 nM, and the K$_1$ value for cocaine displacement of [I$^{125}$] RTI-55 binding was 1740 nM. In the uptake assays, 31,654 had about the same potency at blocking the uptake of [$^3$H] norepinephrine, with an IC$_{50}$ value of 176 nM, as compared to the potency of cocaine (IC$_{50}$ 264 nM).

| | 31,654 | Cocaine |
|---|---|---|
| *Effects of 31,654 on HEK-hDAT, HEK-hSERT and HEK-hNET cells* | | |
| HEK-hDAT cells | | |
| [I$^{125}$] RTI-55 binding K$_1$ (nM) | 26.2 ± 2.5 | 258 ± 23 |
| Hill coefficient | −0.88 ± 0.09 | −0.76 ± 0.05 |
| [$^3$H] Dopamine Uptake IC$_{50}$ (nM) | 301 ± 16 | 276 ± 22 |
| HEK-hSERT cells | | |
| [I$^{125}$] RTI-55 binding K$_1$ (nM) | 255 ± 89 | 343 ± 31 |
| Hill coefficient | −1.16 ± 0.18 | −0.97 ± 0.08 |
| [$^3$H] Serotonin Uptake IC$_{50}$ (nM) | 1233 ± 24 | 301 ± 31 |
| HEK-hNET cells | | |
| [I$^{125}$] RTI-55 binding K$_1$ (nM) | 92 ± 11 | 1740 ± 180 |
| Hill coefficient | −0.59 ± 0.02 | −0.71 ± 0.03 |
| [$^3$H] NE Uptake IC$_{50}$ (nM) | 176 ± 79 | 264 ± 57 |

Numbers represent the means ± SEM from at least three independent experiments, each conducted with duplicate (for binding assays) or triplicate (for uptake assays) determinations. When the K$_1$ or the IC$_{50}$ for the test compound is greater than 10 μM, only two experiments are conducted and no standard error is reported.

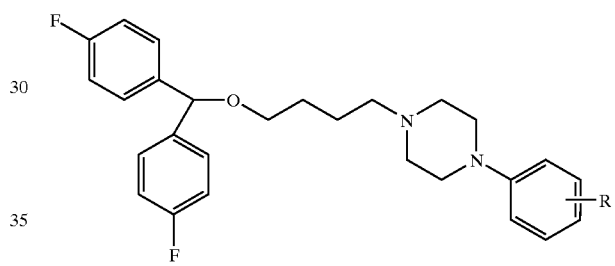

TABLE 3

Binding Affinities and Selectives of (Bisarylmethoxy)butylpiperazine analogs at the DA, 5-HT and NE Transporters Labeled with [I$^{125}$] RTI-55 (Ki ± SD, nM)[a]

| | | Binding (Ki ± SD, nM) | | | | |
|---|---|---|---|---|---|---|
| Compound | R | DAT | SERT | NET | SERT/DAT | NET/DAT |
| 31653 | H | 60.9 ± 6.4 | 51 ± 18 | 203 ± 76 | 0.8 | 3.3 |
| 31626 | 2-Cl | 67 ± 10 | 88 ± 29 | 540 ± 180 | 1.3 | 8.1 |
| 31651 | 3-Cl | 175 ± 71 | 148 ± 62 | 300 ± 70 | 0.8 | 1.7 |
| 31652 | 4-Cl | 50 ± 12 | 33 ± 11 | 380 ± 130 | 0.7 | 7.6 |
| 31654 | 2-OCH$_3$ | 26.2 ± 2.5 | 255 ± 89 | 92 ± 11 | 9.7 | 3.5 |
| 31526 | 2-F | 38.7 ± 5.6 | 30.0 ± 8.4 | 417 ± 34 | 0.8 | 10.8 |
| 31527 | 4-F | 26.5 ± 3.0 | 34 ± 12 | 207 ± 20 | 1.3 | 7.8 |
| 31532 | 3-CF$_3$ | 32.5 ± 4.1 | 222 ± 80 | 221.6 ± 9.7 | 6.8 | 6.8 |
| cocaine | | 258 ± 23 | 343 ± 31 | 1740 ± 180 | | |
| cocaine[b] | | 573 ± 54 | 402 ± 62 | 2040 ± 280 | | |
| cocaine[c] | | 271 ± 65 | 217 ± 23 | 1730 ± 280 | | |

The Ki values of the test ligands were determined in the above assays as described in Methods. Results are average ±SEM of three independent experiments assayed in triplicate.
[b]Cocaine as reference for 3162.
[c]Cocaine as reference for 31526, 31527 and 31532.

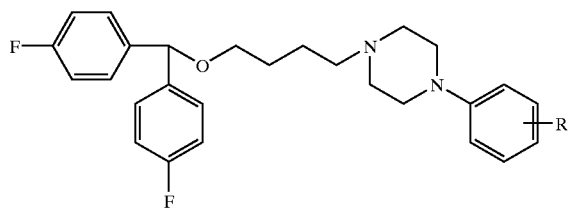

TABLE 4

DA, 5-HT and NE Reuptake Inhibition and Ratios of Reuptake to binding of Bisarylmethoxybutylpiperazine analogs at the DA and 5-HT Transporters (IC$_{50}$ ± SD, nM)[a]

| Com- pound# | R | Reuptake Ihibition (IC$_{50}$ ± SD, nM) | | | Discrim- ination Ratio DAT Binding/ Reuptake |
|---|---|---|---|---|---|
| | | [$^3$H]DA | [$^3$H]-HT | [$^3$H]NE | |
| 31653 | H | 1410 ± 580 | 1020 ± 320 | 56.3 ± 9.4 | 23.2 |
| 31626 | 2-Cl | 328 ± 34 | 119 ± 33 | 299 ± 110 | 4.9 |
| 31651 | 3-Cl | 1670 ± 440 | 920 ± 420 | 189 ± 89 | 9.5 |
| 31652 | 4-Cl | 1170 ± 250 | 320 ± 120 | 390 ± 130 | 23.4 |
| 31654 | 2-OCH$_3$ | 301 ± 16 | 1233 ± 24 | 176 ± 79 | 11.5 |
| 31526 | 2-F | 460 ± 140 | 192 ± 21 | 700 ± 240 | 11.9 |
| 31527 | 4-F | 610 ± 150 | 440 ± 50 | 225 ± 28 | 23.0 |
| 31532 | 3-CF$_3$ | 380 ± 130 | 3300 ± 1300 | 310 ± 100 | 11.7 |
| cocaine | | 276 ± 22 | 301 ± 53 | 264 ± 57 | |

TABLE 4-continued

DA, 5-HT and NE Reuptake Inhibition and Ratios of Reuptake to binding of Bisarylmethoxybutylpiperazine analogs at the DA and 5-HT Transporters (IC$_{50}$ ± SD, nM)[a]

| Com- pound# | R | Reuptake Ihibition (IC$_{50}$ ± SD, nM) | | | Discrim- ination Ratio DAT Binding/ Reuptake |
|---|---|---|---|---|---|
| | | [$^3$H]DA | [$^3$H]-HT | [$^3$H]NE | |
| cocaine[b] | | 237 ± 41 | 348 ± 66 | 190 ± 38 | |
| cocaine[c] | | 278 ± 53 | 189 ± 31 | 209 ± 36 | |

The Ki values of the test ligands were determined in the above assays as described in Methods. Results are average ±SEM of three independent experiments assayed in triplicate.
[b]Cocaine as reference for 31626.
[c]Cocaine as reference for 31526, 31527 and 31532.

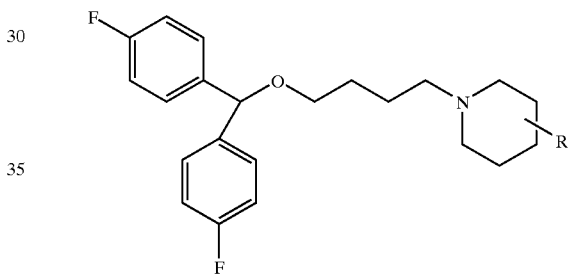

TABLE 5

Binding Affinities and Selectivities of Bisarylmethoxybutylpiperidine analogs at the DA, 5-HR and NE Transporters Labeled with [I$^{125}$]RT-55 (Ki ± SD, nM)[a]

| Compounds | R | Binding (Ki ± SD, nM) | | | | |
|---|---|---|---|---|---|---|
| | | DAT | SERT | NET | SERT/DAT | NET/DAT |
| 31650 | 3-OH | 91 ± 26 | 437 ± 66 | 611 ± 79 | 4.8 | 6.7 |
| 31648 | 4-OH | 124 ± 27 | 423 ± 98 | 610 ± 130 | 3.7 | 5.4 |
| 31628 | 3-CONH$_2$ | 94 ± 42 | 132 ± 26 | 578 ± 52 | 1.4 | 6.1 |
| 31649 | 4-(2-keto-1benzimidazolinyl) | 1.32 ± 0.49 | 3.8 ± 1.0 | 22.2 ± 3.6 | 2.9 | 16.8 |
| cocaine | | 258 ± 23 | 343 ± 31 | 1740 ± 180 | | |
| cocaine[b] | | 573 ± 54 | 402 ± 62 | 2040 ± 240 | | |

[a]The Ki values of the test ligands were determined in the above assays as described in Methods. Results are average ±SEM of three independent experiments assayed in triplicate.
[b]Cocaine as reference for 31628.

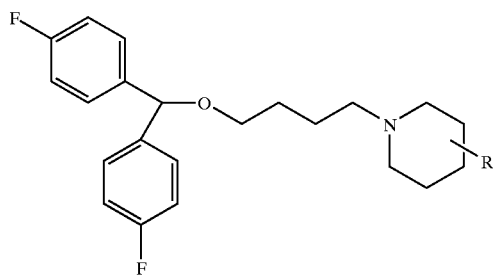

TABLE 6

DA, 5-HT and NE Reuptake Inhibition and Ratios of Reuptake to binding of Bisarylmethoxybutylpiperidine analogs at the DA and 5-HT Transporters (IC$_{50}$ ± SD, nM)$^a$

| Com-pound# | R | Reuptake Inhibition (IC$_{50}$ ± SD, nM) | | | Discrimination Ratio DAT Binding/Reuptake |
|---|---|---|---|---|---|
| | | [$^3$H]DA | [$^3$H]5-HT | [$^3$H]NE | |
| 31650 | 3-OH | 114 ± 28 | 860 ± 10 | 310 ± 110 | 1.3 |
| 31648 | 4-OH | 101 ± 11 | 314 ± 71 | 143 ± 50 | 0.9 |
| 31628 | 3-CONH$_2$ | 56 ± 16 | 203 ± 78 | 158 ± 60 | 0.6 |
| 31649 | 4-(2-keto-1-benzimidazo-linyl) | 426 ± 54 | 570 ± 210 | 132 ± 11 | 323 |
| cocaine | | 276 ± 22 | 301 ± 53 | 264 ± 57 | |
| cocaine | | 237 ± 41 | 348 ± 66 | 190 ± 38 | |

$^a$The Ki values of the test ligands were determined in the above assays as described in Methods. Results are average ±SEM of three independent experiments assayed in triplicate.

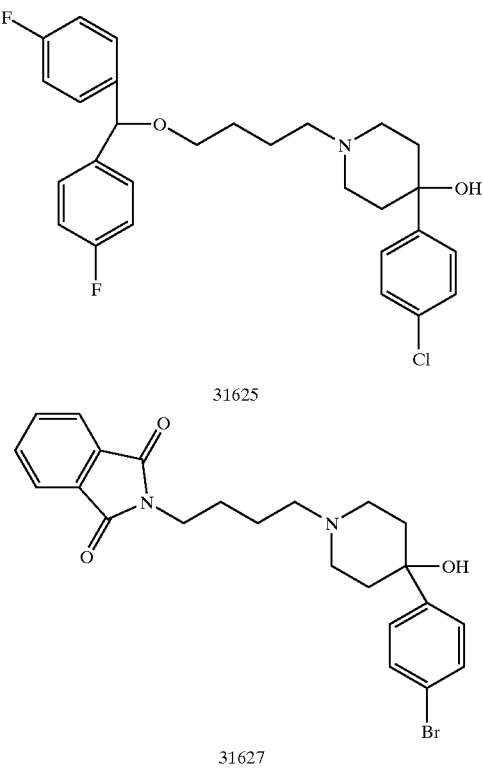

TABLE 7

Binding Affinities and Selectives of Butoxypiperidine analogs at the DA, 5-HT and NE Transporters labeled with [I$^{125}$] RTI-55 (Ki ± SD, nM)$^a$

| | Binding (Ki ± SD, nM) | | | | |
|---|---|---|---|---|---|
| Compound | DAT | SERT | NET | SERT/DAT | NET/DAT |
| 31625 | 4.2 ± 6.4 | >10 μM | 217 ± 16 | 2380 | 51.7 |
| 31627 | >10 μM | 1591 ± 43 | >10 μM | >0.2 | 1 |
| cocaine | 573 ± 54 | 402 ± 62 | 2040 ± 240 | | |

$^a$The Ki values of the test ligands were determined in the above assays as described in Methods. Results are average ±SEM of three independent experiments assayed in triplicate.

TABLE 8

DA, 5-HT and NE Reuptake Inhibition and Ratios of Reuptake to binding of Butoxypiperidine analogs at the DA and 5-HT Transporters (IC$_{50}$ ± SD, nM)$^a$

| Compound# | Reuptake Inhibition (IC$_{50}$ ± SD, nM) | | | Discrimination Ratio DAT Binding/Reuptake |
|---|---|---|---|---|
| | [$^3$H]DA | [$^3$H]5-HT | [$^3$H]NE | |
| 31625 | 400 ± 170 | 10 μM | 800 ± 340 | 95.2 |
| 31627 | >10 μM | 361 ± 68 | >10 μM | |
| cocaine | 237 ± 41 | 348 ± 66 | 190 ± 38 | |

$^a$The Ki values of the test ligands were determined in the above assays as described in Methods. Results are average ±SEM of three independent experiments assayed in triplicate.

What is claimed is:

1. A piperidine dopamine, norepinephrine, or serotonin ligand having the formula:

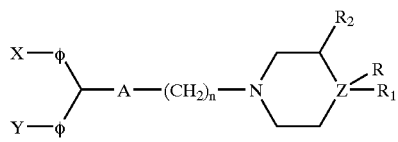

wherein:

A is oxygen or nitrogen; n is an integer of 2 to 6; X and Y are the same or different and are hydrogen, halogen, nitro, alkyl, or halalkyl; Z is carbon or nitrogen; and Φ is phenyl or naphthyl;

R is hydrogen, cyano, hydroxyl, —COOCH3, —CH2OH, or —COOH; R1 is 4-fluorophenyl, 4-chlorophenyl, 4-trifluoromethyl-3-chlorophenyl, 4-bromophenyl, 4-(2keto-1-benzimidazolinyl) or 1-ophenyl 1,3,8-triaspiro[4,5] decan-4-one R2 is hydrogen or

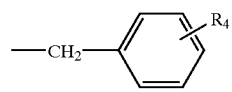

wherein R4 is halo, alkyl, cyano, nitro, alkylnyl, or alkenyl.

2. A compound of the formula:

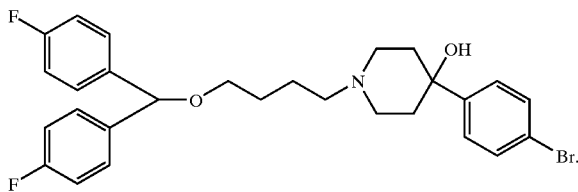

3. The compound of any one of claims 1 or 2 which is labeled with a radionuclide.

4. The compound of claim 3 wherein said radionuclide is 99 mTc.

5. The compound of claim 3 wherein said radionuclide is an iodine isotope.

6. The method for imaging dopamine neurons in a mammal which comprises:
   administering to the mammal an imaging dose of the compound of claim 1 labeled with a radionuclide and detecting binding of the compound in the mammal.

7. The method for imaging dopamine neurons in a mammal which comprises:
   administering to the mammal and imaging dose of the compound of claim 2 labeled with a radionuclide and detecting binding of the compound in the mammal.

8. The method for treating a mammal afflicted with cocaine abuse which comprises:
   administering to the mammal an imaging dose of the compound of claim 1 labeled with a radionuclide and detecting binding of the compound in the mammal.

9. The method for treating a mammal afflicted with cocaine abuse which comprises:
   administering to the mammal an imaging dose of the compound of claim 2 labeled with a radionuclide and detecting binding of the compound in the mammal.

10. The method of treating a mammal afflicted with a neurodegenerated disease characterized by a degeneration of serotonin neurons wherein the disease is selected from Parkinson's disease, brain aging.

11. The method of treating an mammal afflicted with a neurodegenerated disease characterized by a degeneration of seratonin neurons which comprises:
    administering to the mammal an effective amount of the compound of claim 2.

* * * * *